(12) United States Patent
Campbell et al.

(10) Patent No.: US 11,407,969 B2
(45) Date of Patent: Aug. 9, 2022

(54) SYSTEM AND METHOD FOR GENERATING BIOLOGICAL TISSUE

(71) Applicant: Yale University, New Haven, CT (US)

(72) Inventors: Stuart Campbell, Madison, CT (US);
Jonas Schwan, New Haven, CT (US);
Andrea Kwaczala, Suffield, CT (US);
Thomas Ryan, Denver, CO (US);
Daniel Jacoby, Madison, CT (US);
Yibing Qyang, Guilford, CT (US);
Lorenzo Sewanan, Hollis, NY (US);
Ronald Ng, Mission Viejo, CA (US);
Jeffery Alexander Clark, Columbus, OH (US)

(73) Assignee: Yale University, New Haven, CT (US)

( * ) Notice: Subject to any disclaimer, the term of this patent is extended or adjusted under 35 U.S.C. 154(b) by 171 days.

(21) Appl. No.: 15/883,381

(22) Filed: Jan. 30, 2018

(65) Prior Publication Data
US 2018/0216057 A1 Aug. 2, 2018

Related U.S. Application Data

(60) Provisional application No. 62/452,055, filed on Jan. 30, 2017.

(51) Int. Cl.
*C12M 1/32* (2006.01)
*C12M 1/34* (2006.01)
*C12M 3/00* (2006.01)
*G01N 33/50* (2006.01)
*C12M 1/42* (2006.01)

(52) U.S. Cl.
CPC .......... *C12M 23/46* (2013.01); *C12M 21/08* (2013.01); *C12M 23/12* (2013.01); *C12M 23/42* (2013.01); *C12M 23/48* (2013.01); *C12M 35/02* (2013.01); *C12M 35/04* (2013.01); *C12M 41/00* (2013.01); *G01N 33/5005* (2013.01)

(58) Field of Classification Search
CPC ...... C12M 21/08; C12M 23/12; C12M 23/42; C12M 23/46; C12M 23/48; C12M 35/02; C12M 35/04; C12M 41/00; G01N 33/5005
See application file for complete search history.

(56) References Cited

U.S. PATENT DOCUMENTS

2008/0076170 A1\* 3/2008 Annala ................. C12M 25/04
435/297.4

FOREIGN PATENT DOCUMENTS

PL       119188 U1 \*  1/2012

OTHER PUBLICATIONS

Georgiou et al. (Biomaterials 34 (2013) 7335-7343) (Year: 2013).\*

(Continued)

*Primary Examiner* — Liban M Hassan
(74) *Attorney, Agent, or Firm* — Riverside Law LLP

(57) ABSTRACT

The present invention relates in part to devices, systems, and methods for the production and characterization of engineered tissue constructs. The devices and methods generate decellularized tissue constructs that can be recellularized using donor cells for high-throughput studies of organ physiology, and/or organ pathology. The devices and methods can be used with the systems to mechanically and electrically stimulate the engineered tissue constructs under culture or physiological conditions to detect and assess the presence and degree of any organ pathologies.

9 Claims, 25 Drawing Sheets
Specification includes a Sequence Listing.

(56) References Cited

OTHER PUBLICATIONS

East et al., "Tissue Engineering: Part A vol. 16, No. 10, 2010". (Year: 2010).*
A. S. Hoffman, 2002, "Hydrogels for biomedical applications." Adv. Drug Del. Rev. 43, 3-12.
Badulos, O. et al. "ISL1 cardiovascular progenitor cells for cardiac repair after myocardial infarction." JCI Insight, 2016, 1:1-17.
Bian, W., et al. Nature Protocols, "Mesoscopic hydrogel molding to control the 3D geometry of bioadificial muscle tissues. ." 2009, 4:1522-1534.
Birket, M. J. et al. "Contractile Defect Caused by Mutation in MYBPC3 Revealed under Conditions Optimized for Human PSC-Cardiomyocyte Function." Cell Rep, 2015, 13:733-745.
Black, L. D., et al. "Cell-induced alignment augments twitch force in fibrin gel-based engineered myocardium via gap junction modification." Tissue Engineering Part A, 2009, 15: 3099-3108.
Boudou, T. et al. "A Microfabricated Platform to Measure and Manipulate the Mechanics of Engineered Cardiac Microtissues." Tissue Engineering Part A, 2012, 18:910-919.
Cashman, T. J., et al. "Human Engineered Cardiac Tissues Created Using Induced Pluripotent Stem Cells Reveal Functional Characteristics of BRAF-Mediated Hypedrophic Cardiomyopathy." PLoS ONE, 2016 11: e0146697 (17 pages).
Costa, K. D., Lee, E. J. & Holmes, J. W. Creating alignment and anisotropy in engineered head tissue: role of boundary conditions in a model three-dimensional culture system. Tissue Eng. 2003, 9, 567-577.
Dong, S. J. et al., "Independent effects of preload, afterload, and contractility on left ventricular torsion." Am. J. Physiol. 277, 1999:H1053-60.
Eschenhagen, T., et al. "Physiological aspects of cardiac tissue engineering." Am J Physiol Head Circ Physiol, 2012, 303:H133-H143.
Feigl, E. O. & Fry, D. L. "Intramural Myocardial Shear During the Cardiac Cycle." Circ Res, 1964, 14:536-540.
Feinberg, A. W. et al. "Controlling the contractile strength of engineered cardiac muscle by hierarchal tissue architecture." Biomaterials, 2012, 33:5732-5741.
Ford, S. J., et al. "Effects of R92 mutations in mouse cardiac troponin T are influenced by changes in myosin heavy chain isoform." J Mol Cell Cardiol, 2012, 53:542-551.
Frank, D. et al., "Gene Expression Pattern in Biomechanically Stretched Cardiomyocytes. Evidence for a Stretch-Specific Gene Program." Hypertension, 2008, 51: 309-318.
Gaborit, F. et al., "Association between left ventricular global longitudinal strain and natriuretic peptides in outpatients with chronic systolic head failure." BMC Cardiovasc Disord, 2015, 15: 92 (8 pages).
Godier-Furnémont, A. F. G. et al. "Physiologic force-frequency response in engineered heart muscle by electromechanical stimulation." Biomaterials, 2015, 60:82-91.
Grosberg, A., et al."Ensembles of engineered cardiac tissues for physiological and pharmacological study: heart on a chip." Lab Chip, 2011, 11:4165-4173.
Hinson, J. T. et al. "Titin mutations in iPS cells define sarcomere insufficiency as a cause of dilated cardiomyopathy." Sci, 2015, 349:982-986.
Hirt, M. N. et al. "Functional improvement and maturation of rat and human engineered heart tissue by chronic electrical stimulation." J Mol Cell Cardiol, 2014, 74:151-161.
Hirt, M. N. et al. "Increased afterload induces pathological cardiac hypertrophy: a new in vitro model . . . " Basic Res Cardiol, 2012, 107:307-16.
Hirt, M. N., et al. "Cardiac Tissue Engineering: State of the Art." Ciro Res, 2014 114:354-367.
Hoshijima, M. "Mechanical stress-strain sensors embedded in cardiac cytoskeleton: Z disk, titin, and associated structures." Am J Physiol Heart Circ Physiol, 2006, 290:H1313-25.
Huebsch, N. et al. "Miniaturized iPS-Cell-Derived Cardiac Muscles for Physiologically Relevant Drug Response Analyses." Sci Rep, 2016, 6:24726 (12 pages).
Law, C., et al. "Extremely High Brain Natriuretic Peptide Does Not Reflect the Severity of Heart Failure." Congest Heart Fail, 2010, 16:221-225.
Lee, E. J., et al. "Remodeling of Engineered Tissue Anisotropy in Response to Altered Loading Conditions. ." Annals of Biomedical Engineering, 2008, 36:1322-1334.
Legrice, I. J., et al. "Transverse Shear Along Myocardial Cleavage Planes Provides a Mechanism for Normal Systolic Wall Thickening." Circ Res, 1995, 77:182-193.
Lin, D. H. & Yin, F. C. "A multiaxial constitutive law for mammalian left ventricular myocardium in steady-state barium contracture or tetanus." J Biomech Eng, 1998, 120:504-517.
Ma, S. P. & Vunjak-Novakovic, G. "Tissue-Engineering for the Study of Cardiac Biomechanics." J Biomech Eng, 2016, 138: 021010 (14 pages).
McCain, M. L. & Parker, K. K. "Mechanotransduction: the role of mechanical stress, myocyte shape, and cytoskeletal architecture on cardiac function." Pflugers Arch—Eur J Physiol, 2011, 462:89-104.
Milani-Nejad, N. & Janssen, "Small and large animal models in cardiac contraction research: advantages and disadvantages." P. M. Pharmacol. Ther., 2014, 141:235-249.
Moreno-Gonzalez, A. et al. "Cell therapy enhances function of remote non-infarcted myocardium." J Mol Cell Cardiol, 2009, 47:603-613.
Morgan, K. Y. & Black, L. D. "Investigation into the effects of varying frequency of mechanical stimulation in a cycle-by-cycle manner on engineered cardiac construct function." J Tissue Eng Regen Med,2014, doi: 10.1002/term.1915 (12 pages).
Mulieri, L. A., et al. "Altered myocardial force-frequency relation in human heart failure." Circulation, 1992, 85:1743-1750.
Nishikimi, T., et al., "The role of natriuretic peptides in cardioprotection." Cardiovasc Res, 2006, 69:318-328.
Pong, T. et al. "Hierarchical architecture influences calcium dynamics in engineered cardiac muscle." Experimental Biology and Medicine, 2011, 236:366-373.
Radisic, M. et al. "Oxygen gradients correlate with cell density and cell viability in engineered cardiac tissue." Biotechnol. Bioeng., 2006, 93:332-343.
Raman, S., et al. "Effect of muscle dimensions on trabecular contractile performance under physiological conditions." Pflugers Arch—Eur J Physiol, 2006, 451: 625-630.
Schwan et al. 2016, "Anisotropic engineered heart tissue made from laser-cut decellularized myocardium." Scientific Reports vol. 6, Article No. 32068 (12 pages).
Schwan, J. & Campbell, S. G. "Prospects for In Vitro Myofilament Maturation in Stem Cell-Derived Cardiac Myocytes." Biomark Insights, 2015, 10:91-103.
Simon, D. D., et al. "Mechanical Restrictions on Biological Responses by Adherent Cells within Collagen Gels." Journal of the Mechanical Behavior of Biomedical Materials 2012, 14:216-226.
Tulloch, N. L. et al. "Growth of Engineered Human Myocardium With Mechanical Loading and Vascular Coculture . . ." Circ Res, 2011,109:47-59.
Turnbull, I. C. et al. "Advancing functional engineered cardiac tissues toward a preclinical model of human myocardium." The FASEB Journal, 2014, 28:644-654.
W. E. Hennink and C. F. van Nostrum, 2002, "Novel crosslinking methods to design hydrogel" Adv. Drug Del. Rev. 54, 13-36.
Wang, Y. et al. "Genome Editing of Human Embryonic Stem Cells and Induced Pluripotent Stem Cells With Zinc Finger Nuclease for Cellular Imaging." Circ Res, 2012, 111: 1494-1503.
Yang, X. et al. "Tri-iodo-l-thyronine promotes the maturation of human cardiomyocytes-derived from induced pluripotent stem cells." J Mol Cell Cardiol, 2014, 72:296-304.
Zimmermann, W. H. et al. "Tissue Engineering of a Differentiated Cardiac Muscle Construct." Circ Res, 2001, 90:223-230.

* cited by examiner

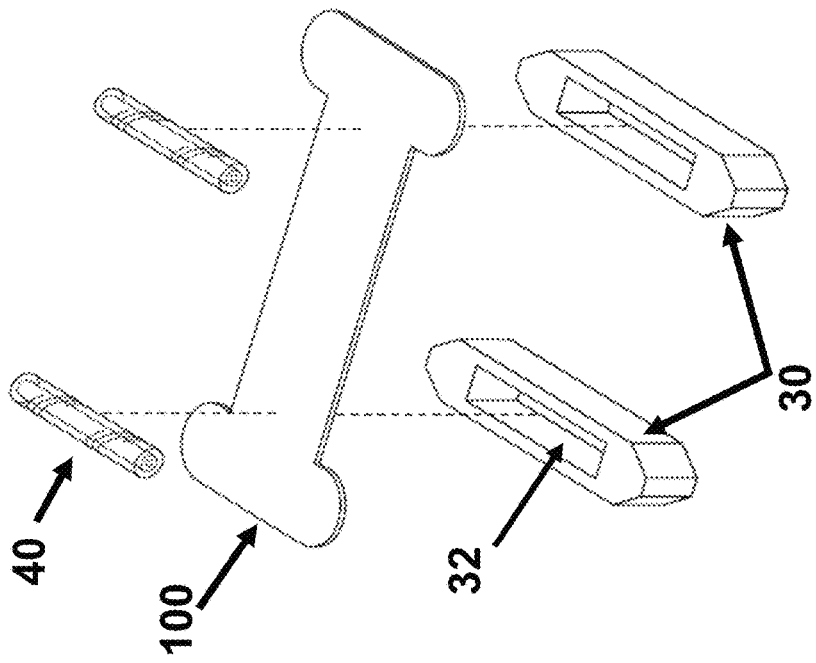
Figure 1B
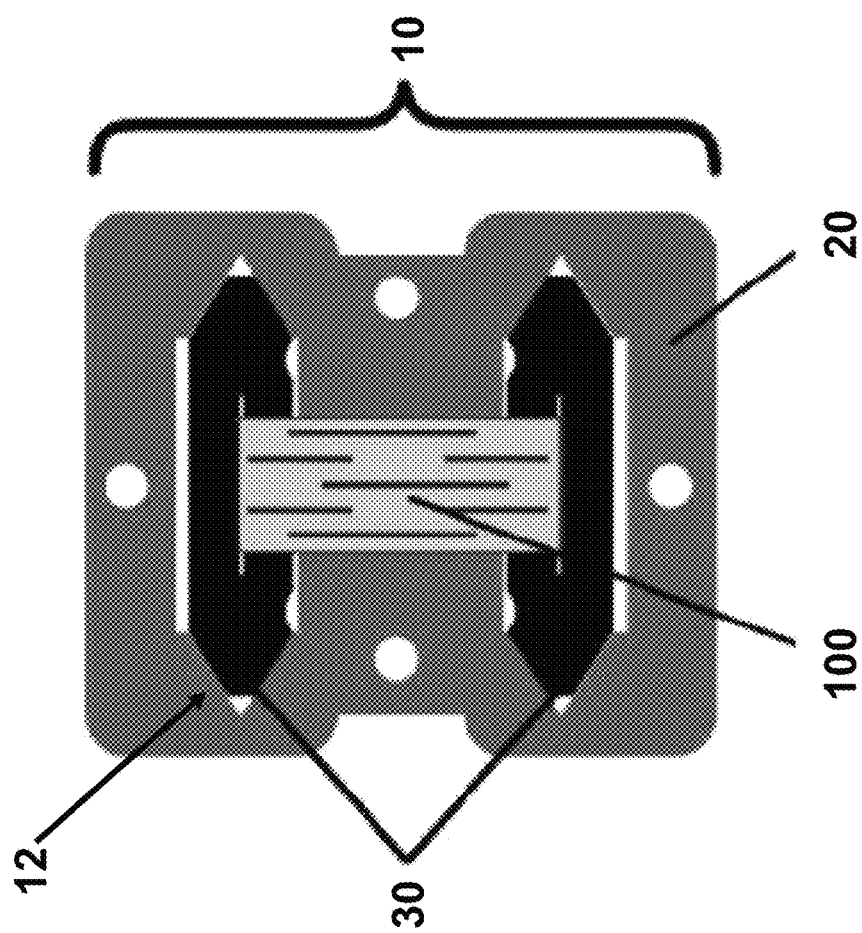
Figure 1A
Figure 1A – Figure 1B

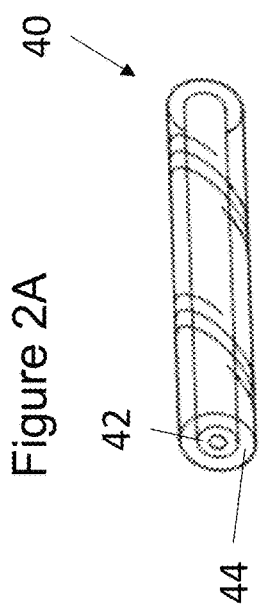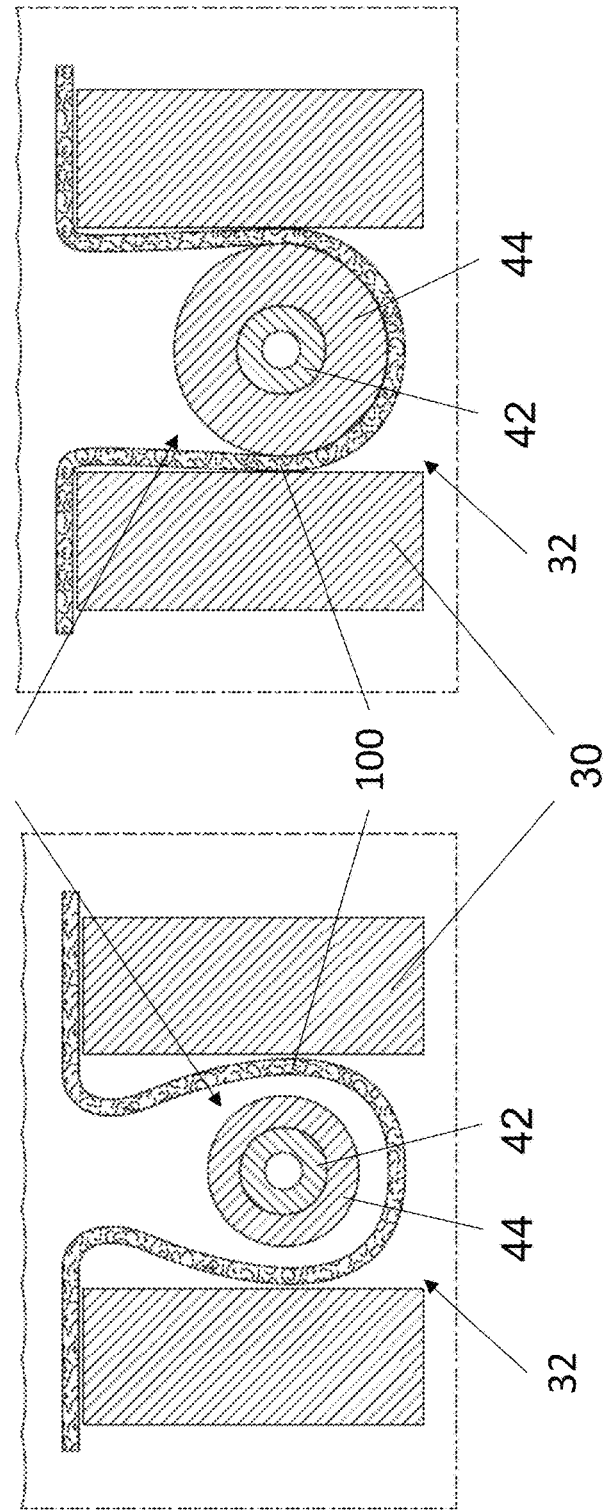

Figure 2D
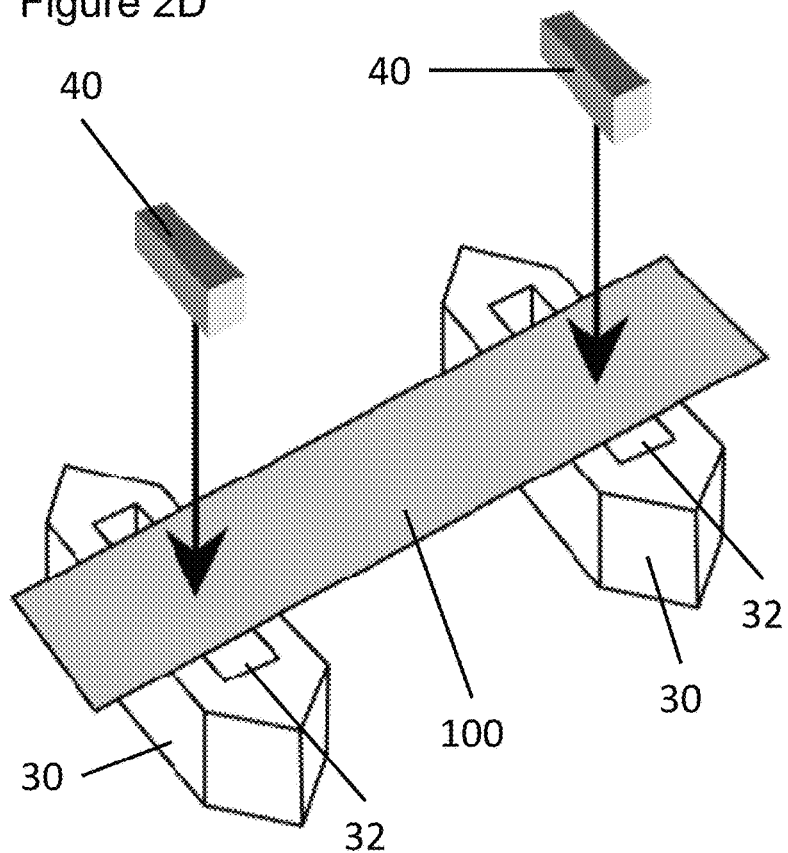
Figure 2E
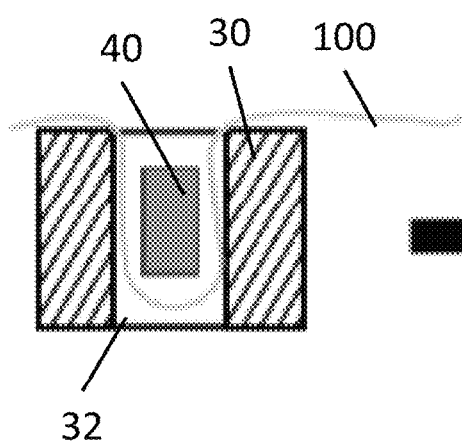
Figure 2F
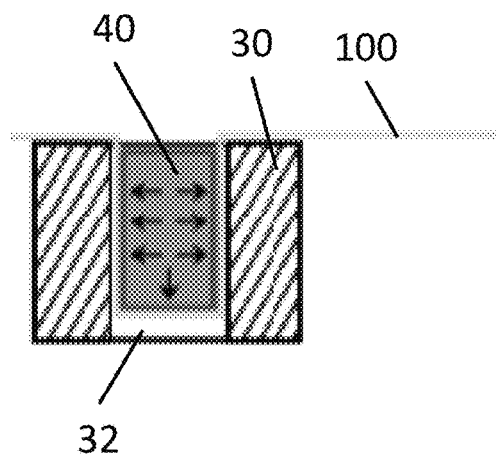
Figure 2D – Figure 2F

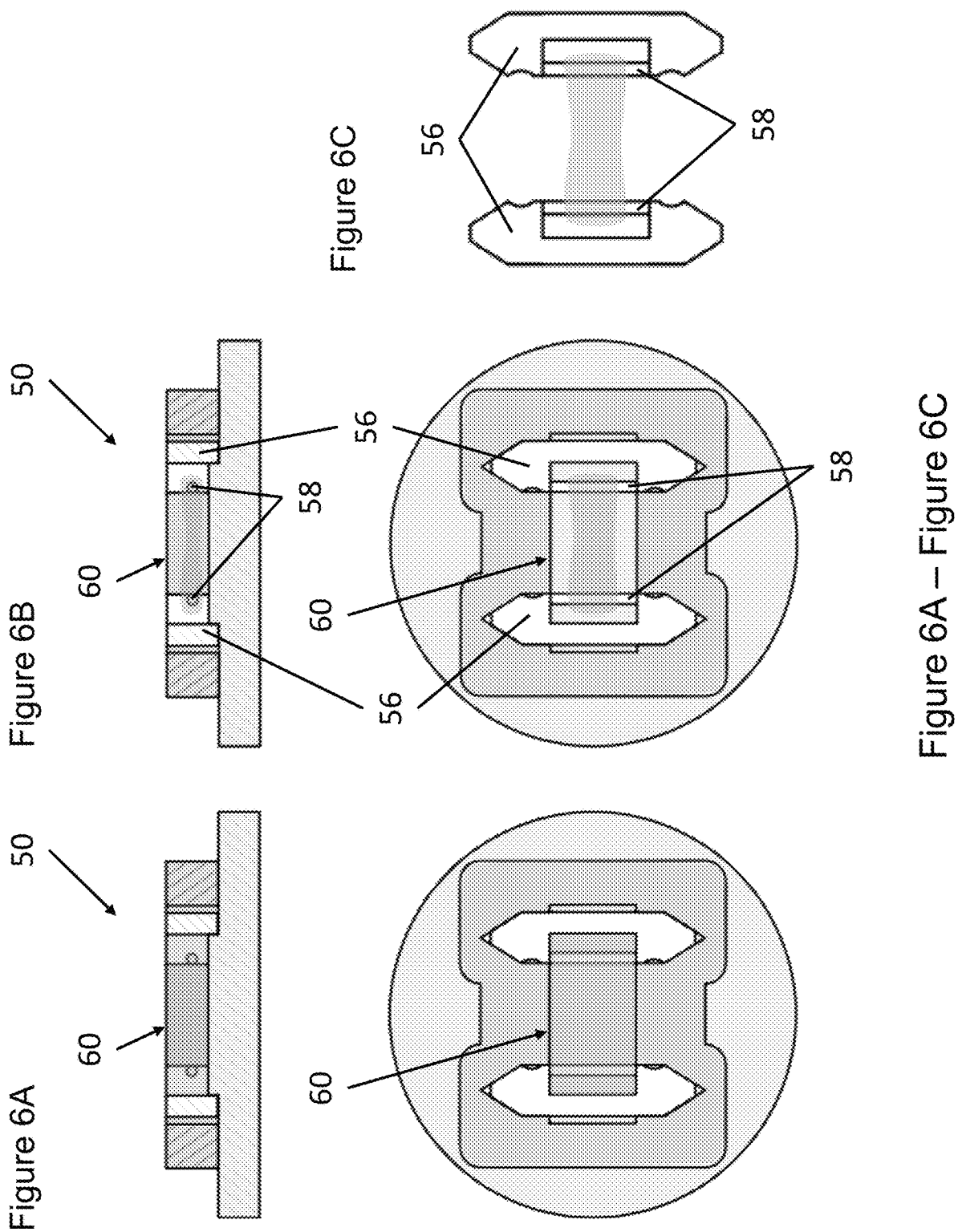

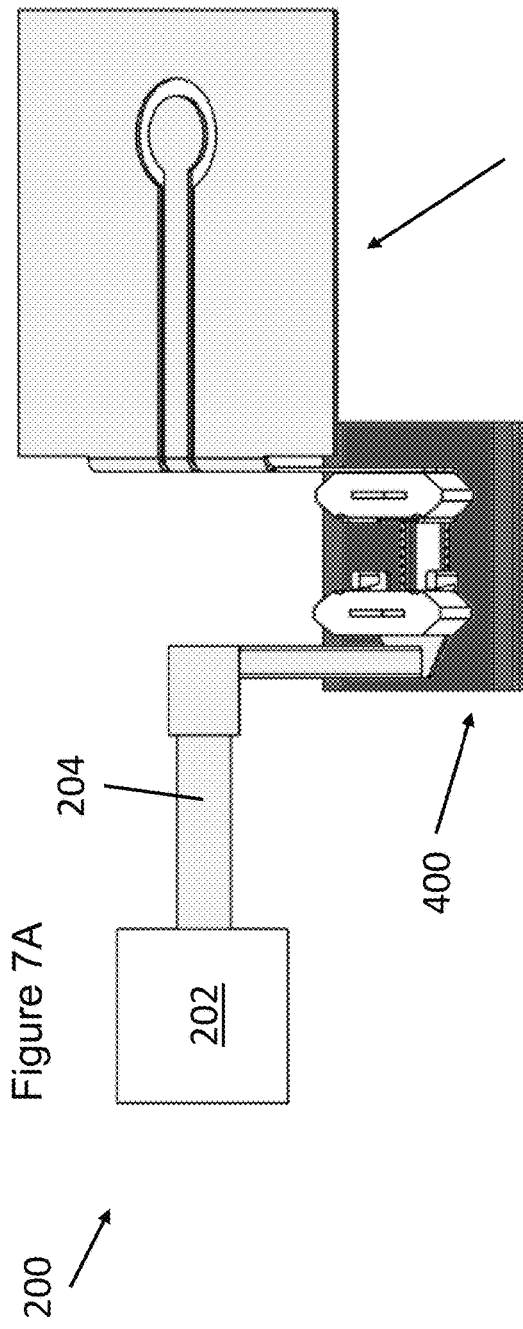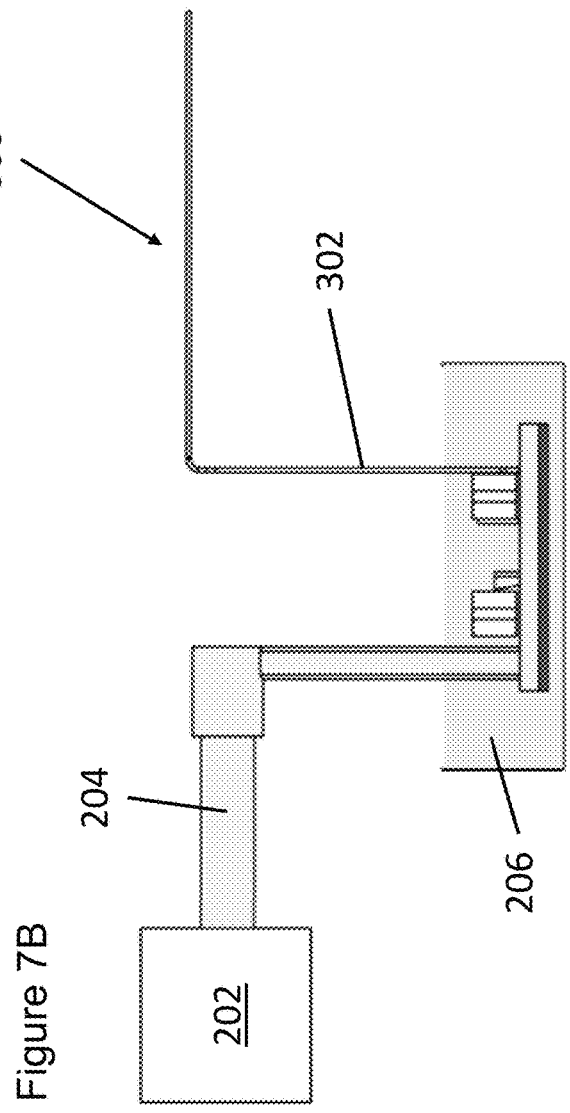

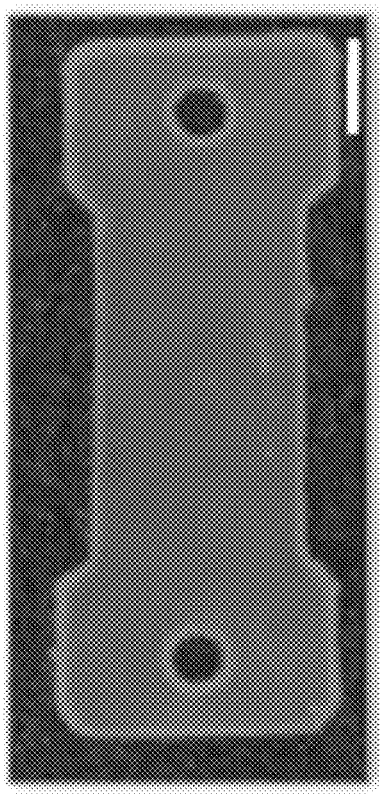
Figure 11A
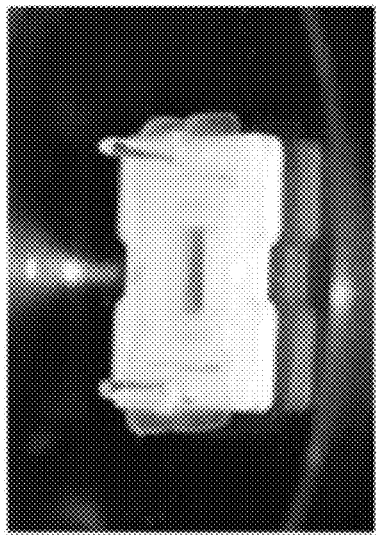
Figure 11B
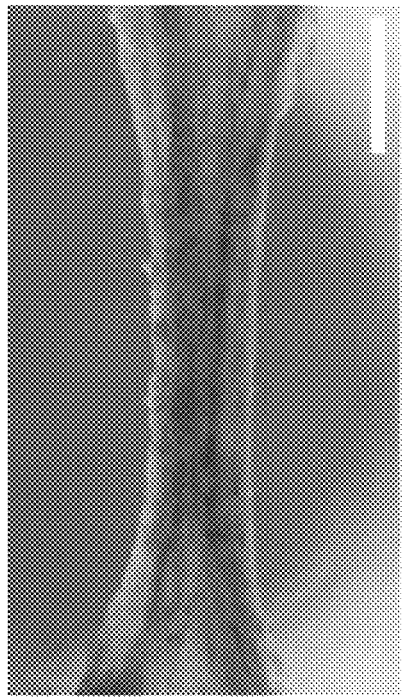
Figure 11D
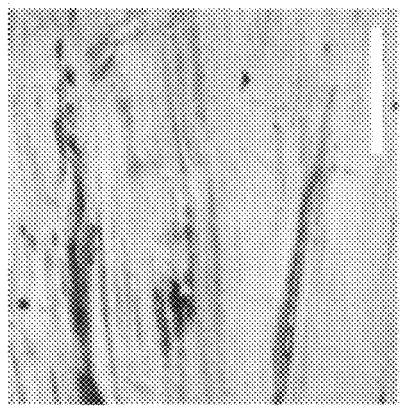
Figure 11C
Figure 11A - Figure 11D Figure 12A
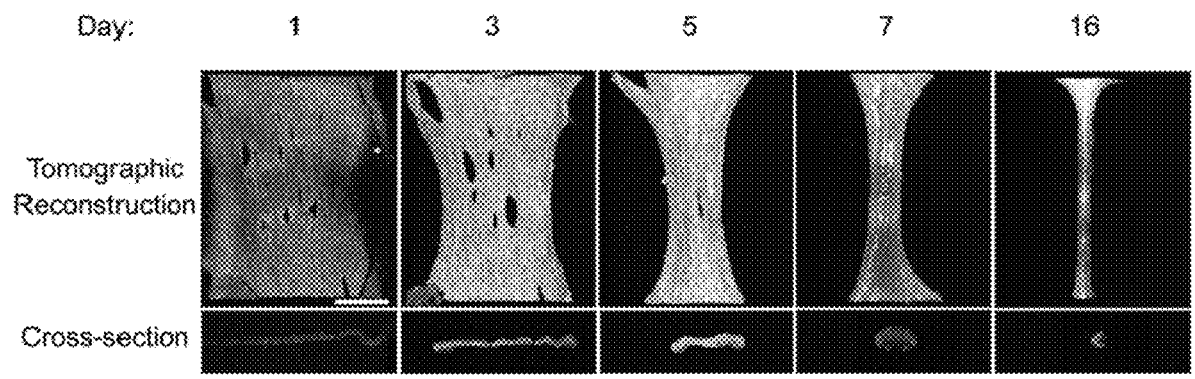
Figure 12B
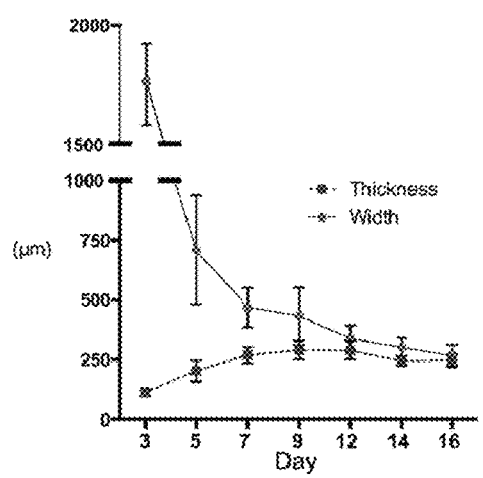
Figure 12C
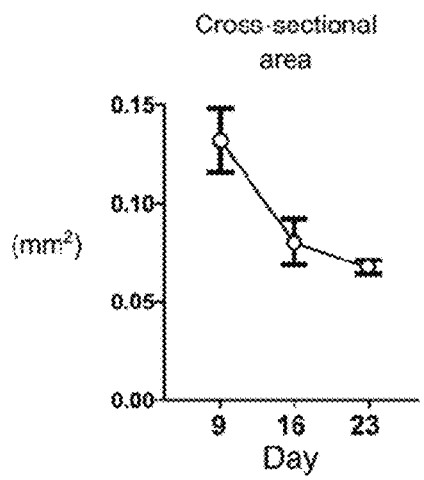
Figure 12D
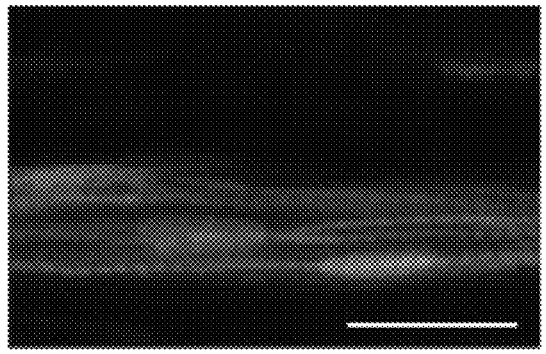
Figure 12E
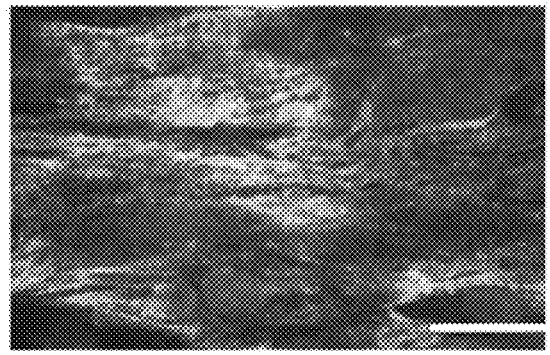
Figure 12A - Figure 12E

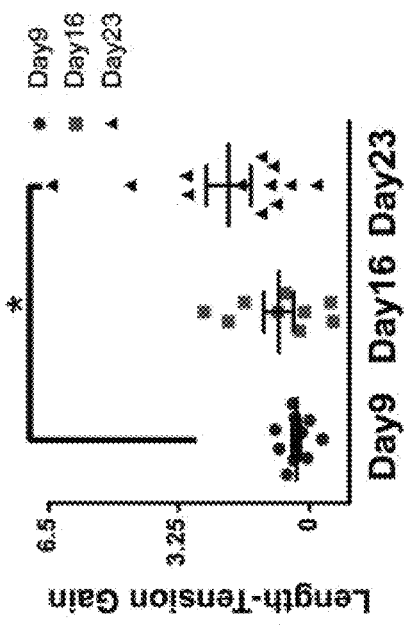
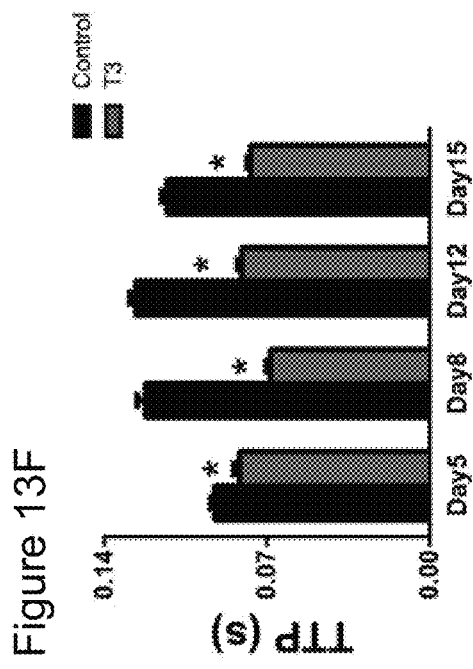
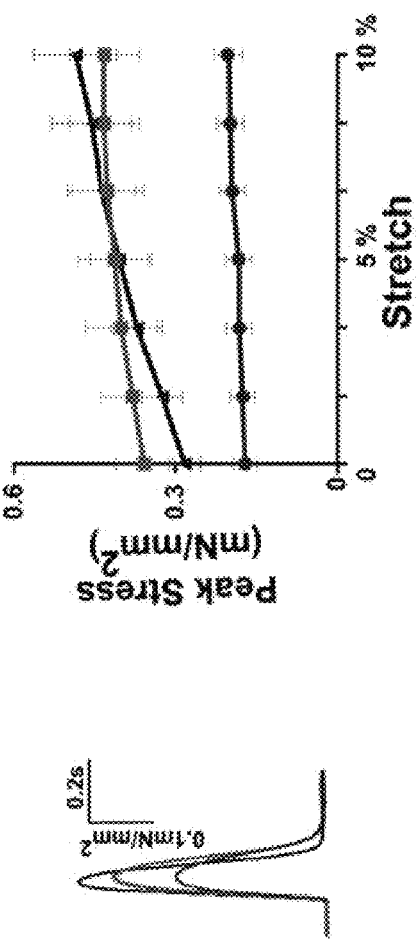
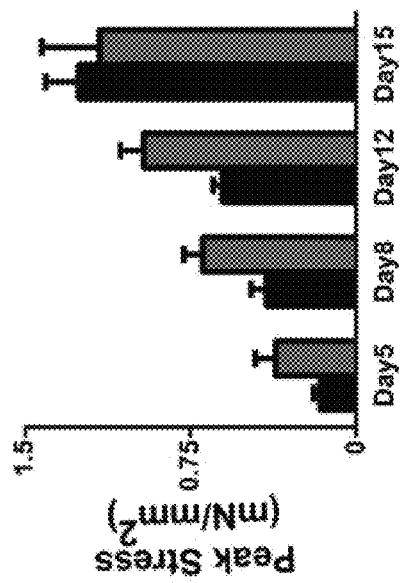
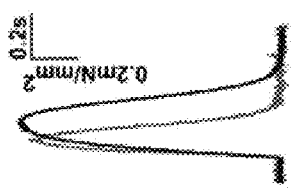
Figure 13A – Figure 13F

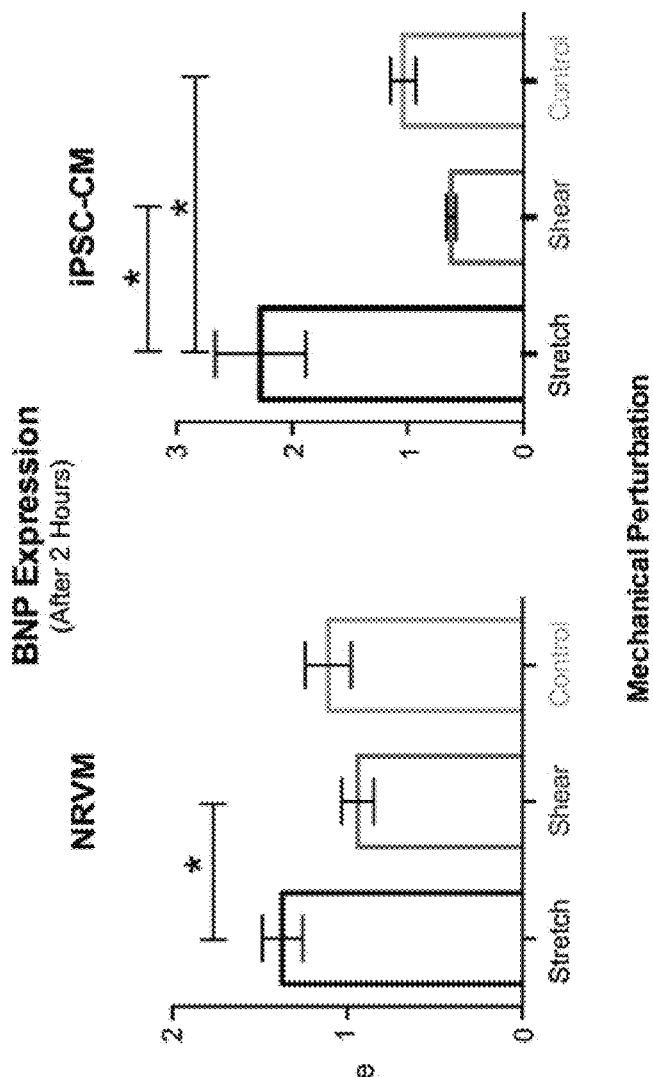
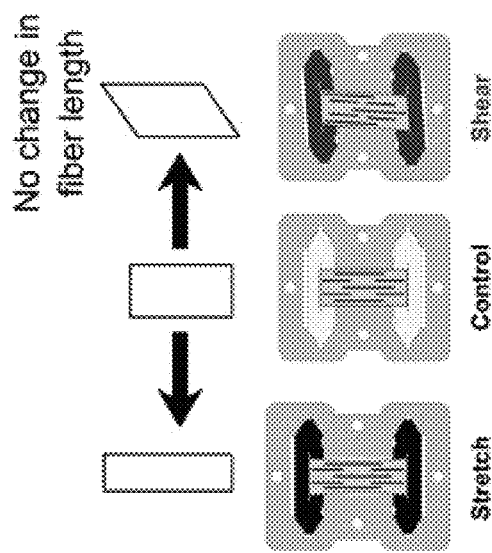
Figure 15A
Figure 15B
Figure 15A – Figure 15B

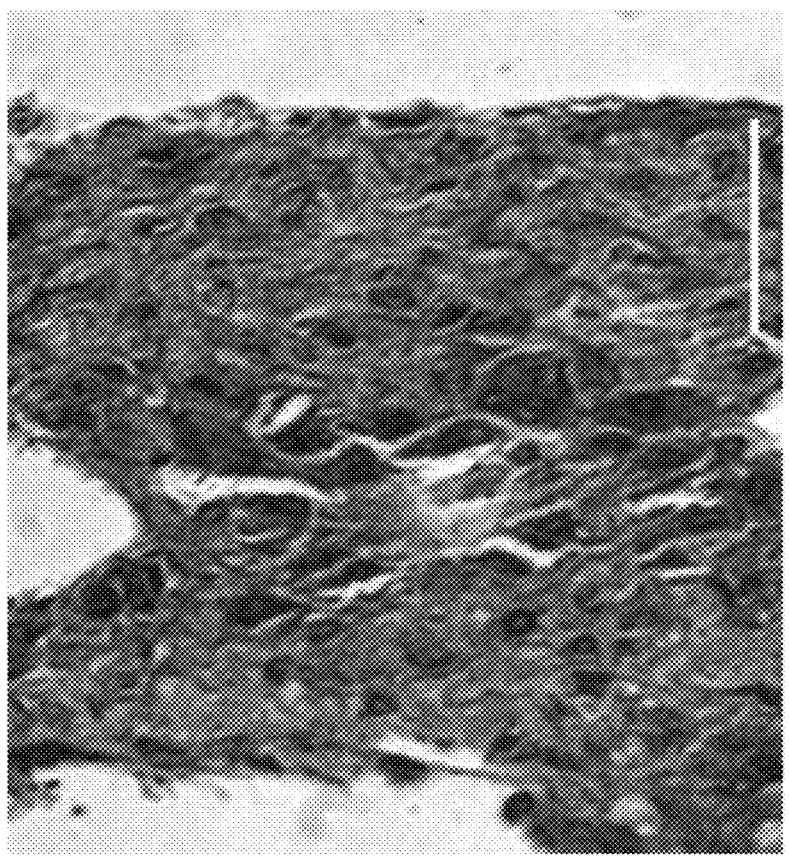
Figure 17B
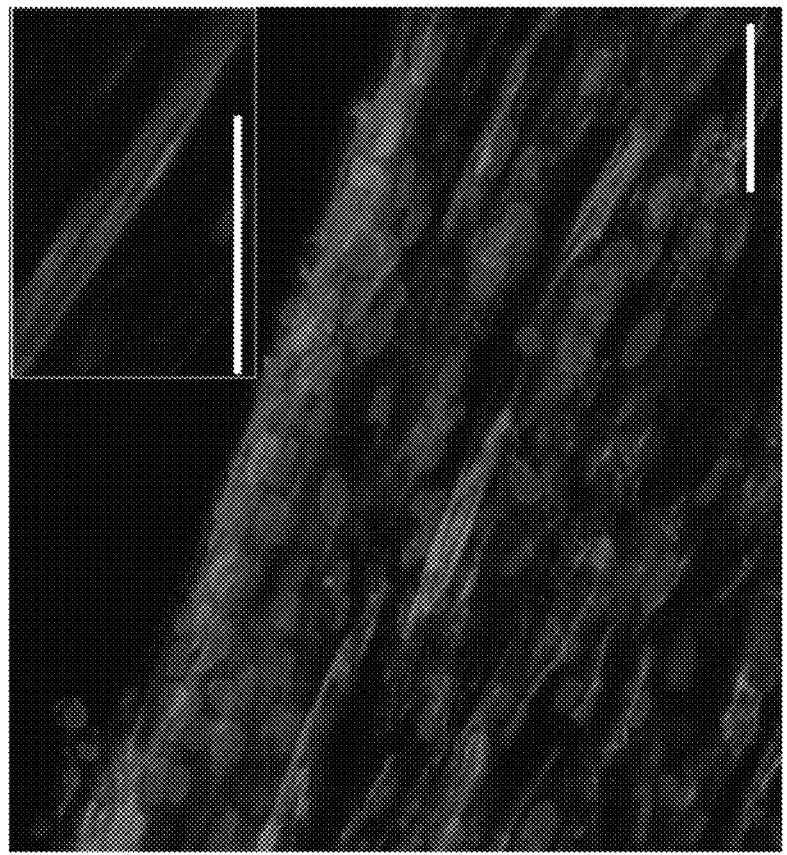
Figure 17A
Figure 17A – Figure 17B

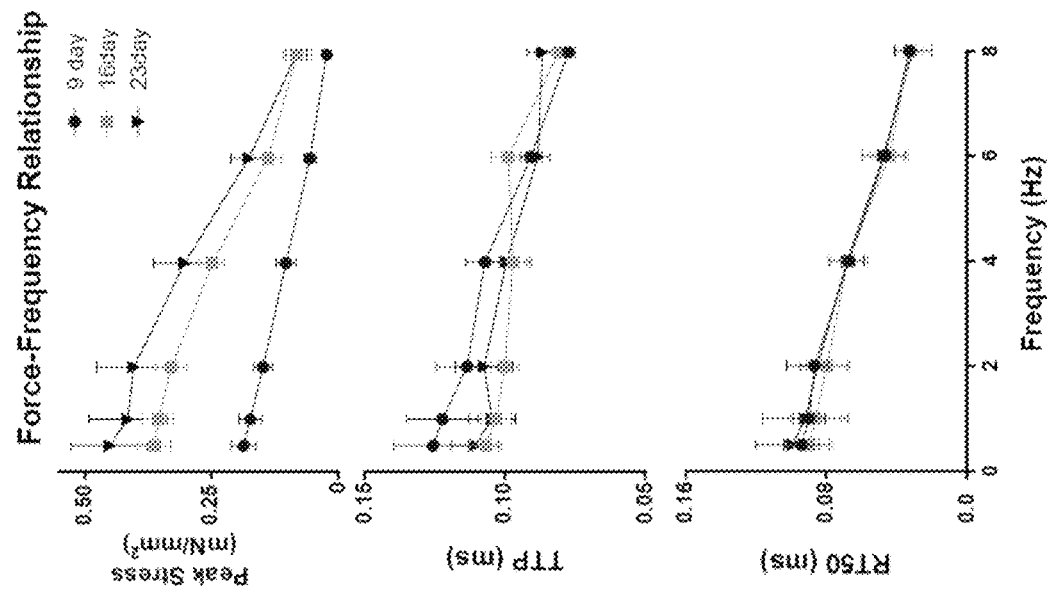
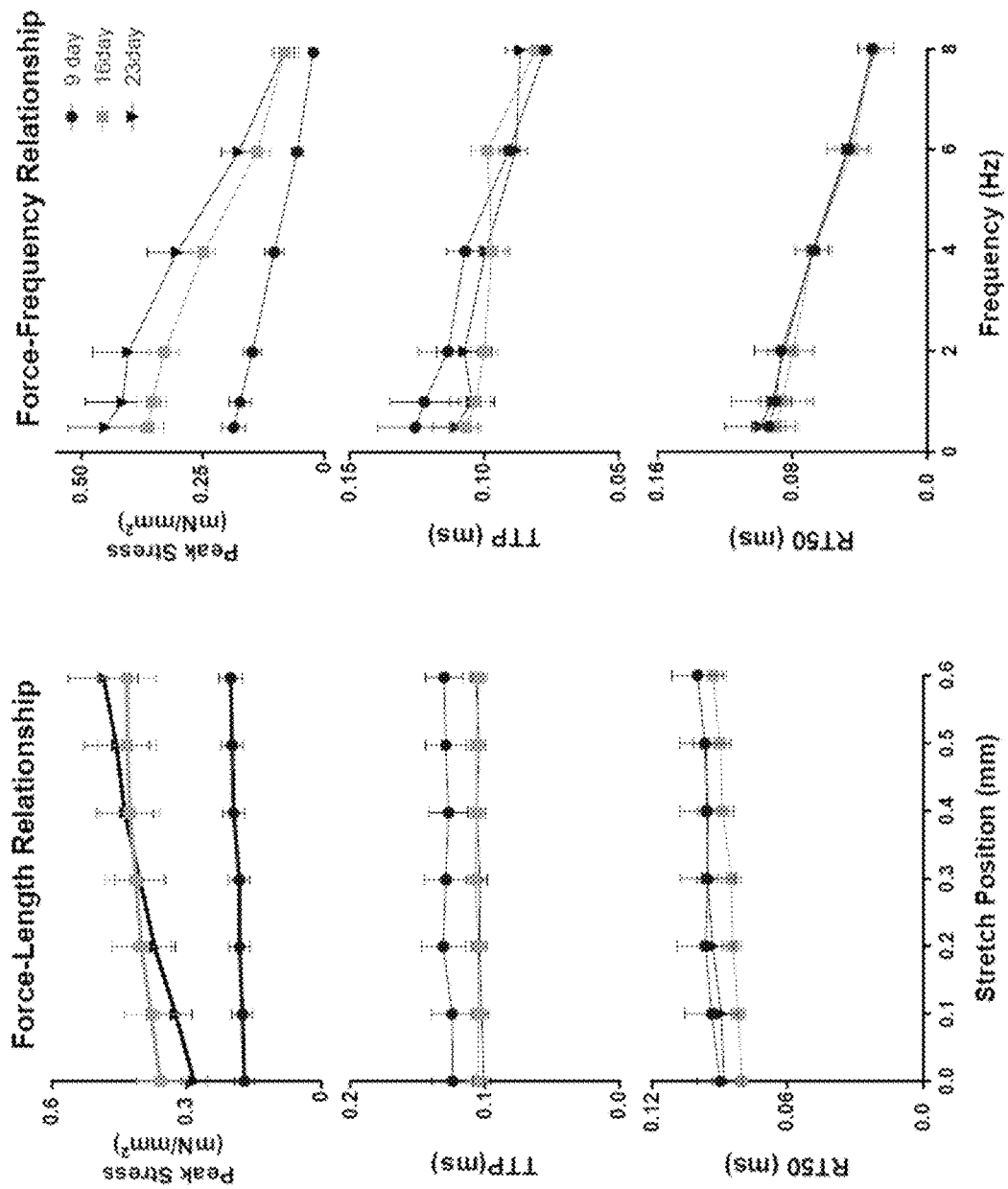
Figure 18A
Figure 18B
Figure 18A – Figure 18B

Figure 20A
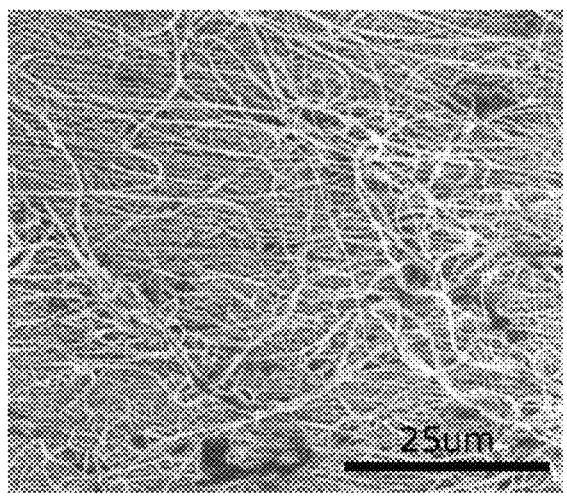
Figure 20B
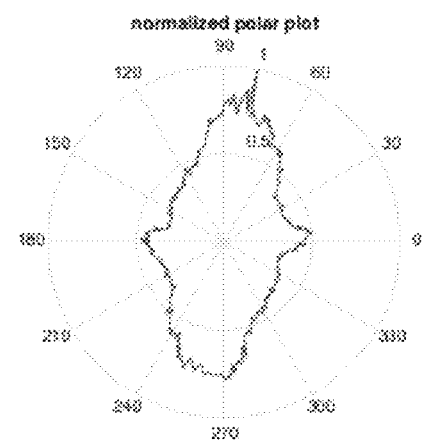
Figure 20C
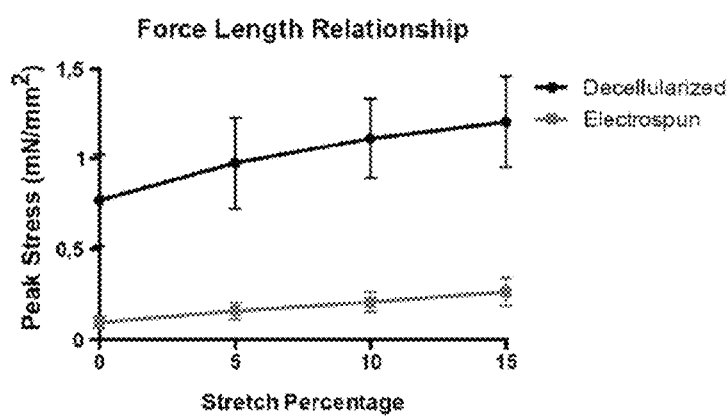
Figure 20D
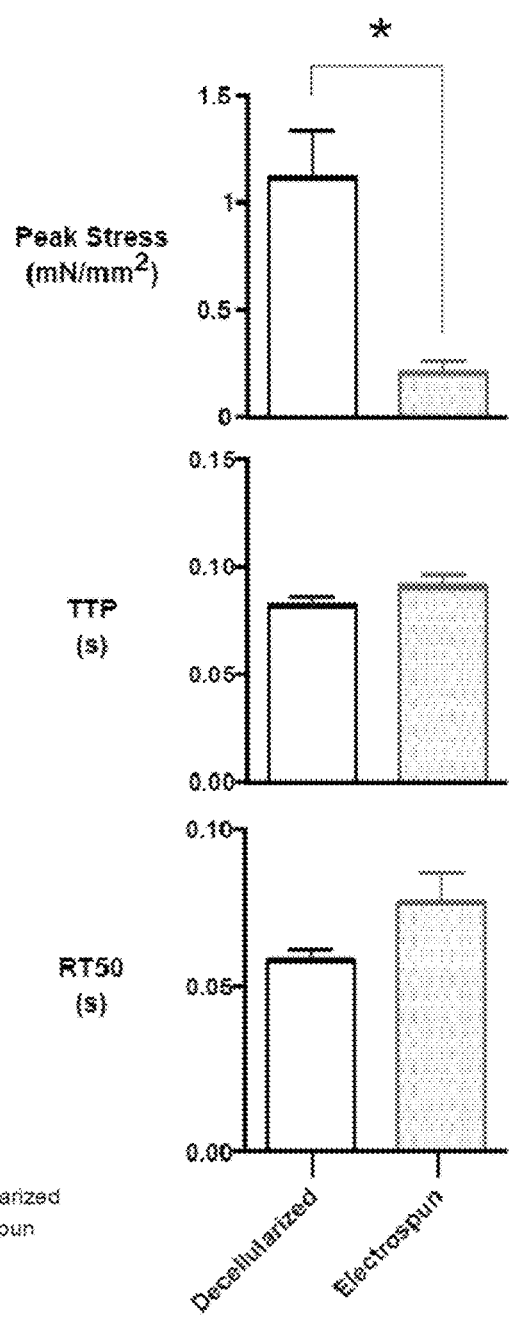
Figure 20A – Figure 20D

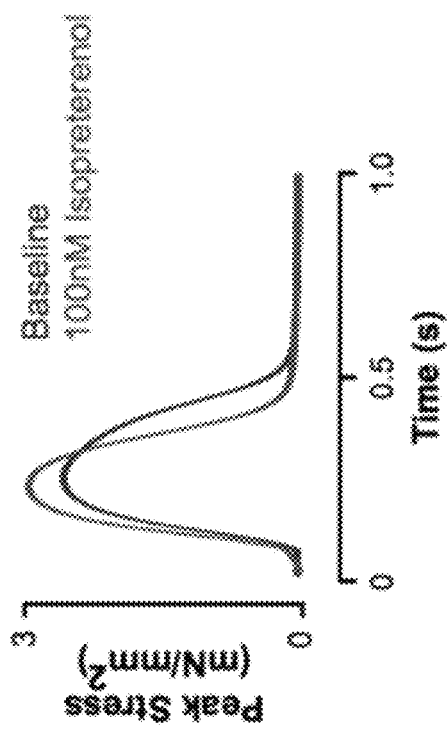
Figure 21A
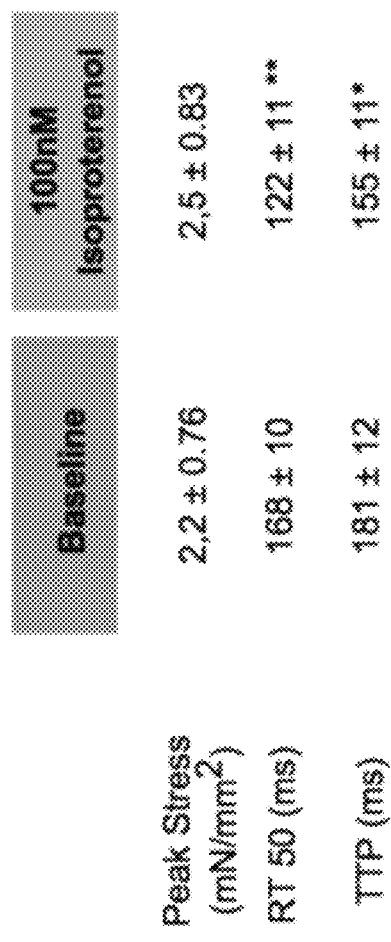
Figure 21B
Figure 21A – Figure 21B

Figure 22A
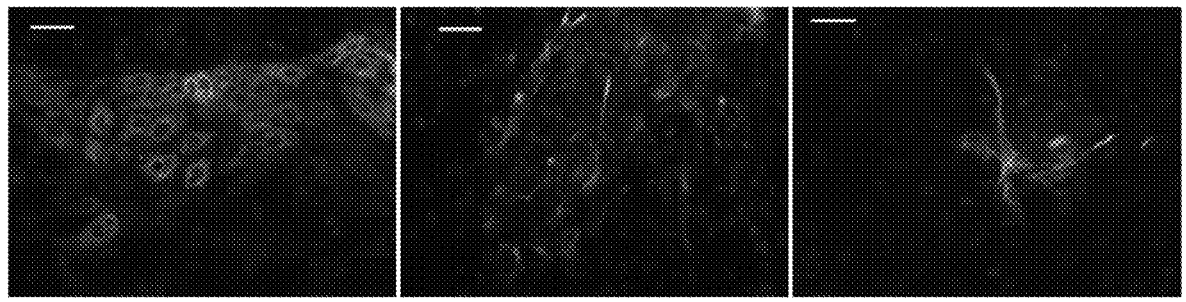
Figure 22B
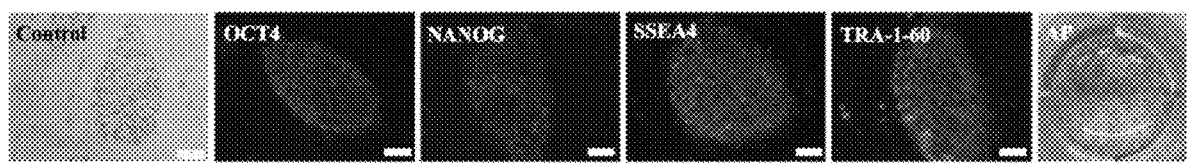
Figure 22C
Figure 22A – Figure 22C

| Control | | Stretch | | Shear | |
|---|---|---|---|---|---|
| NRVM | iPSC-CM | NRVM | iPSC-CM | NRVM | iPSC-CM |
| 1,407 | 0,994 | 1,324 | 1,241 | 1,290 | 0,718 |
| 0,711 | 1,006 | 1,782 | 0,911 | 0,745 | 0,518 |
| 1,949 | 0,781 | 1,156 | 3,963 | 1,040 | 0,597 |
| 0,660 | 1,274 | 0,960 | 1,485 | 1,000 | 0,654 |
| 0,777 | 0,653 | 1,230 | 2,181 | 1,233 | |
| 1,563 | 1,540 | 0,784 | 5,756 | 0,591 | |
| 1,162 | 0,652 | 2,168 | 3,543 | 0,779 | |
| 0,551 | 0,302 | 1,221 | 2,819 | 0,839 | |
| 2,240 | | 1,937 | 0,524 | 1,385 | |
| 0,920 | | 2,421 | | 1,476 | |
| 0,485 | | 2,042 | | 0,813 | |
| 1,475 | | 0,790 | | 0,432 | |
| 1,454 | | 1,170 | | 1,993 | |
| 1,016 | | 1,071 | | 1,709 | |
| 0,544 | | 1,191 | | 0,484 | |
| 0,842 | | 0,945 | | 0,501 | |
| | | 1,070 | | 0,689 | |
| | | 1,446 | | 0,665 | |
| | | | | 0,620 | |
| | | | | 0,580 | |
| | | | | 0,547 | |
| | | | | 1,292 | |

Figure 23

SEQ ID NO 1: GAPDH Forward Primer

5'-TGTTGCCATC AATGACCCCT T-3'

SEQ ID NO 2: GAPDH Reverse Primer

5'-CTCCACGACG TACTCAGCG-3'

SEQ ID NO 3: BNP Forward Primer

5'-ACCGCAAAAT GGTCCTCTAC-3'

SEQ ID NO 4: BNP Reverse Primer

5'-GCCAGGACTT CCTCTTAATG-3'

SEQ ID NO 5: ANP Forward Primer

5'-ATCTGATGGA TTTCAAGAAC C-3'

SEQ ID NO 6: ANP Reverse Primer

5'-CTCTGAGACG GGTTGACTTC-3'

Figure 24

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence

```
<220> FEATURE:
<223> OTHER INFORMATION: GAPDH Forward Primer

<400> SEQUENCE: 1
tgttgccatc aatgaccect t                                              21

<210> SEQ ID NO 2
<211> LENGTH: 19
<212> TYPE: DNA
<213> ORGANISM: Artificial Sequence
<220> FEATURE:
<223> OTHER INFORMATION: GAPDH Reverse Primer

<400> SEQUENCE: 2
ctccacgacg tactcagcg                                                 19

<210> SEQ ID NO 3
<211> LENGTH: 20
<212> TYPE: DNA
<213> ORGANISM: Artificial Sequence
<220> FEATURE:
<223> OTHER INFORMATION: BNP Forward Primer

<400> SEQUENCE: 3
accgcaaaat ggtcctctac                                                20

<210> SEQ ID NO 4
<211> LENGTH: 20
<212> TYPE: DNA
<213> ORGANISM: Artificial Sequence
<220> FEATURE:
<223> OTHER INFORMATION: BNP Reverse Primer

<400> SEQUENCE: 4
gccaggactt cctcttaatg                                                20

<210> SEQ ID NO 5
<211> LENGTH: 21
<212> TYPE: DNA
<213> ORGANISM: Artificial Sequence
<220> FEATURE:
<223> OTHER INFORMATION: ANP Forward Primer

<400> SEQUENCE: 5
atctgatgga tttcaagaac c                                              21

<210> SEQ ID NO 6
<211> LENGTH: 20
<212> TYPE: DNA
<213> ORGANISM: Artificial Sequence
<220> FEATURE:
<223> OTHER INFORMATION: ANP Reverse Primer

<400> SEQUENCE: 6
ctctgagacg ggttgacttc                                                20
```

SYSTEM AND METHOD FOR GENERATING BIOLOGICAL TISSUE

CROSS-REFERENCE TO RELATED APPLICATIONS

This application claims priority to U.S. Provisional Application No. 62/452,055, filed Jan. 30, 2017, the contents of which are incorporated by reference herein in its entirety.

BACKGROUND OF THE INVENTION

Inherited cardiomyopathies are life-threatening disorders that occur in as many as one in 250 Americans. Families typically learn of the disease when a family member experiences sudden cardiac death, almost always without any previous warning signs. Cardiomyopathies are the leading cause of sudden death in young athletes, but symptoms can also appear for the first time in middle age. Once a person is discovered to have the condition, the primary task for healthcare providers is to prevent sudden death in all at-risk family members, either by prescription medication or an implantable cardioverter/defibrillator (ICD). These interventions are costly and come with risks of their own. Hence, it is critical to accurately assess sudden death risk in each family member. The current state of the art is to screen family members using genetic markers. However, this approach suffers from two serious drawbacks: (1) meaningful genetic markers are only found in ~50% of patients, meaning that in half of all families there is no possibility of genetic risk assessment; and (2) even when a genetic marker is thought to be present, variable penetrance of the gene defect is observed, such that not all individuals harboring the gene mutation end up having life-threatening symptoms.

Thus, there is a need in the art for systems and methods for the production of biologically relevant organ constructs from patient tissue that recapitulate native phenotypes for better diagnostics. The present invention satisfies this unmet need.

SUMMARY OF THE INVENTION

In one aspect, the present invention provides a cassette device for securing a tissue scaffold, the device comprising: a frame having a top surface with at least two clip slots in the top surface; and at least two clips sized to fit within the clip slots of the top surface of the frame; wherein the at least two clips are configured to secure a tissue scaffold to the frame when the clips are positioned in the clip slots such that the tissue scaffold is suspended between each of the clips.

In one embodiment, each clip comprises a slit sized to fit a tab, and wherein the tab fits over a section of the tissue scaffold within the slit. In one embodiment, the tabs have a cylindrical shape. In one embodiment, the tabs are constructed from an expandable material. In one embodiment, the expandable material comprises a hydrogel. In one embodiment, the tabs further include an inner core comprising a length of PTFE tube.

In one embodiment, the tissue scaffold comprises a sample of decellularized tissue. In one embodiment, the tissue scaffold comprises cardiac tissue. In one embodiment, the cardiac tissue is ventricular wall tissue.

In one embodiment, the clips each comprise a lateral cutout facing towards a centrally positioned mold space in the top surface of the frame, each clip further comprising a bar spanning the width of the lateral cutout. In one embodiment, the tissue scaffold is a hydrogel-construct formed by an amount of a cell-laden hydrogel compacted around the bar of each clip.

In another aspect, the present invention relates to a cell-seeding bath, comprising: a substrate having a top surface; one or more wells embedded in the top surface of the substrate, each well sized to fit an inverted frame of the scaffold device of the present invention; and an indent embedded in the bottom of each of the wells, each indent sized to fit a tissue scaffold suspended between each of the clips of the scaffold device of the present invention.

In another aspect, the present invention relates to a bioreactor system comprising: a linear actuator connected by an arm to a first clip holder; a force measuring component connected by an arm to a second clip holder; and a reservoir having an electrode component positioned underneath the first and second clip holders; wherein the first clip holder and the second clip holder are each configured to hold a clip of the device of the present invention. In one embodiment, the first and second clip holder each comprise an electrode.

In one embodiment, the force measuring component comprises: a substantially planar plate having a cutout and at least one sensor positioned above and below the cutout; and a first arm segment joined near one end to an edge of the plate; and a second arm segment connected to the end of the first arm segment near its joining to the plate, the second arm segment being positioned within the cutout of the plate and in-plane with the plate and having at least one conductive element positioned between the at least one sensor of the plate; wherein the first arm segment is capable of bending relative to the plate to move the second arm segment out-of-plane with the plate.

In one embodiment, the electrode component comprises: a substantially planar circuit board; at least two electrodes positioned along opposing edges of the circuit board; and an electrode array positioned at the center of the circuit board, the electrode arraying comprising a plurality of electrodes arranged in a grid.

In another aspect, the present invention relates to a method of phenotyping generated tissue, the method comprising: securing opposing ends of a decellularized tissue scaffold into a first clip and a second clip; seeding and culturing donor cells into the scaffold; attaching the first and second clip to the first and second clip holder of the system of the present invention; applying at least one instance of stimulation to the scaffold; and recording scaffold responses to the at least one instance of stimulation.

In one embodiment, the at least one instance of stimulation includes mechanical stimulation applied by the linear actuator and the scaffold response is measurable by the force measuring component. In one embodiment, the at least one instance of stimulation includes electrical stimulation applied by the electrode component and the scaffold response is measurable by the electrode component.

In one embodiment, the decellularized tissue is cardiac tissue. In one embodiment, the cardiac tissue is ventricular wall tissue. In one embodiment, the donor cells are selected from the group consisting of human embryonic stem cells and human induced pluripotent stem cells. In one embodiment, the cells are differentiated under mechanical loading. In one embodiment, the scaffold responses indicate the donor cells originate from a subject having a cardiomyopathy selected from the group consisting of: hypertrophic cardiomyopathy, dilated cardiomyopathy, restrictive cardiomyopathy, arrhythmogenic right ventricular dysplasia, and unclassified cardiomyopathy.

BRIEF DESCRIPTION OF THE DRAWINGS

The following detailed description of the invention will be better understood when read in conjunction with the appended drawings. It should be understood, however, that the invention is not limited to the precise arrangements and instrumentalities of the embodiments shown in the drawings.

FIG. 1A through FIG. 1B depict an exemplary cassette and respective parts for attaching a precision cut sample of tissue for seeding and straining. FIG. 1A depicts a top view of the exemplary cassette assembly comprising a clip assembly, a frame, and a tissue specimen. FIG. 1B is an exploded view of two clips, a precision cut cardiac tissue specimen, and two tabs to secure the tissue specimen to the clips.

FIG. 2A through FIG. 2F depict exemplary locking mechanisms of a clip assembly for securing a tissue specimen. FIG. 2A depicts a perspective view of a tab comprising an inner tube core and an outer hydrogel layer. FIG. 2B depicts the initial loading state of a tissue specimen into a slit of a representative clip. FIG. 2C depicts the secure final state of a tissue specimen wherein the clip is submerged in an aqueous solution and the outer hydrogel layer of the tab has expanded, securing the tissue specimen to the clip. FIG. 2D shows the locking mechanism using molded tabs of partially dry PEG hydrogel. FIG. 2E depicts a cross-sectional view of the initial loading state of a tissue specimen into a slit of a representative clip. FIG. 2F depicts a cross-sectional view of the secure final state of a tissue specimen wherein the tab has expanded after exposure to an aqueous solution, securing the tissue specimen to the clip.

FIG. 4A is a perspective view of the cassette mounted on a pedestal. FIG. 4B is a top-down view of the cassette mounted on a pedestal. FIG. 4C is a cross-sectional view of the cassette mounted on a pedestal.

FIG. 5A depicts a schematic diagram of the key steps in producing laser-cut engineered heart tissues (EHTs). FIG. 5B depicts a tissue culture cassette consisting of PTFE clips and a frame assembly used to culture EHTs. FIG. 5C is a schematic of the clamping method used to anchor a decellularized scaffold into a clip by means of a small plastic tab. FIG. 5D is a computer rendering of a mechanical testing apparatus. An EHT attached to culture clips at opposite ends is gripped by two claw-like extensions, one of which is attached to a force transducer (right) that measures uniaxial force. FIG. 5E is a representative force trace recorded from an EHT containing neonatal rat ventricular myocytes (NRVMs) under 0.5 Hz electrical stimulation at 37° C. bath temperature (scale bar, 200 milliseconds).

FIG. 6A through FIG. 6C depict a hydrogel-based construct being generated using an exemplary cassette. FIG. 6A depicts cross-sectional and top-down views of an amount of a cell-laden hydrogel placed within the mold space of the cassette. FIG. 6B depicts cross-sectional and top-down views of the hydrogel having been compacted by the cells to form a hydrogel-based construct. FIG. 6C depicts the clips removable from the cassette with the hydrogel-based construct intact.

FIG. 7A and FIG. 7B depict an exemplary bioreactor. FIG. 7A is a perspective view of a bioreactor with a clip assembly attached to an actuator and a force measuring device, the clip assembly being suspended above a circuit board. FIG. 7B is a side view of the bioreactor with the clip assembly and the circuit board immersed in a fluid reservoir.

FIG. 8A is a perspective view of a force measuring device attached to a partially shown clip and EHT assembly. FIG. 8B is a side view of a force measuring device attached to a partially shown clip and EHT assembly, the force measuring device being depicted with upper and lower sensors visible.

FIG. 11A through FIG. 11D depict intermediate steps in a tissue preparation protocol. FIG. 11A depicts a laser-cut porcine scaffold prior to decellularization (scale bar, 2 mm). FIG. 11B depicts the use of laser-cut holes within the scaffold to temporarily mount tissue onto removable posts placed into holes cut into either end of a culture frame. FIG. 11C is an image of native myocardial fiber orientation (running left to right) which can be seen by light micrograph after decellularization (scale bar, 250 μm). FIG. 11D depicts the results of seeding a decellularized porcine scaffold with NRVMs and 16 days in culture, wherein EHTs form hour-glass shapes and exhibit spontaneous beating (scale bar, 1 mm).

FIG. 12A through FIG. 12E depict the results of experiments demonstrating matrix remodeling and histology in seeded EHTs. FIG. 12A is an image of optical coherence tomography (OCT) showing 3D reconstructions of EHTs (first row) formed by stacking serial cross-sectional images (second row) (scale bar, 1 mm). FIG. 12B illustrates how OCT was used to follow EHT thickness and width between 3 and 16 days post-seeding. FIG. 12C illustrates mean cross-sectional area assessed in 9-, 16-, and 23-day old EHTs. FIG. 12D depicts fluorescent staining for actin filaments (phalloidin, red) and nuclei (DAPI, blue) showing the formation of NRVMs into rod-shaped cells within the scaffold after 16 days of culture. Striations indicate the formation of sarcomeres (scale bar, 25 μm). FIG. 12E depicts staining for cardiac Troponin T (green) and Connexin 43 (red) of an EHT seeded with human embryonic stem cell-derived cardiomyocytes. Note the formation of gap junctions between neighboring cardiomyocytes after 16 days in culture (scale bar, 25 μm).

FIG. 13A through FIG. 13F depict the results of experiments demonstrating physiological function in laser-cut EHTs. All results were obtained from NRVMs seeded into laser-cut decellularized porcine myocardium. FIG. 13A depicts representative twitch stress records after culture for 9 (blue, n=11), 16 (red, n=8), and 23 days (black, n=12). FIG. 13B illustrates the effect of culture time and uniaxial stretch on twitch stress. FIG. 13C depicts the effect of culture time on the slope of the length-stress relationship in EHTs (increase in $mN/mm^2$ per unit engineering strain ANOVA, Tukey post hoc, $*p<0.05$). FIG. 13D depicts the results of representative twitch stress records from 15 day-old EHTs cultured in control media (black) or in media containing thyroid hormone T3 (teal). FIG. 13E depicts the effect of T3 treatment (treated n=10 vs. non-treated n=12) on peak stress through repeated measurements of EHTs after 5, 8, 12, and 15 days in culture. FIG. 13F depicts the effect of T3 treatment on time elapsed between stimulus to peak stress (Time-to-peak, TTP, repeated measures ANOVA, *p<0.01).

FIG. 14A is a schematic illustrating longitudinal (black clips) vs. transverse (green clips) fiber alignment of tissue (pink). FIG. 14B depicts representative twitch stress records of EHTs from longitudinal (n=6) or transverse (n=7) fiber alignments after 9 days in culture. FIG. 14C depicts the effect of fiber orientation on peak stress (Student's t-test, **p<0.001), on time elapsed between stimulus to peak stress (Time-to-peak, TTP, Student's t-test, *p<0.05) and on time elapsed between peak stress to 50% peak stress (Relaxation-time 50, RT50, n.s.). FIG. 14D and FIG. 14E each depict decellularized scaffolds under light microscope showing longitudinal (FIG. 14D) and transverse (FIG. 14E) fiber alignment.

FIG. 15A and FIG. 15B illustrate opposing effects of static shear and stretch loading in seeded EHTs. FIG. 15A is a schematic illustrating normal 10% stretch (black, n=18 (NRVM) & n=9 (iPSC-CM)), 10% shear stretch (purple, n=22 (NRVM) & n=4 (iPSC-CM)) or no stretch (grey, n=16 (NRVM) & n=8 (iPSC-CM))) applied to EHTs. FIG. 15B shows the effect of 2 hours of these regimes on brain natriuretic peptide (BNP) expression (normalized to GAPDH, 1-way ANOVA, *p<0.05).

FIG. 16A shows that laser-cut decellularized myocardium serves as a viable scaffold for several cardiomyocyte sources, including neonatal rats, human embryonic stem cells (hESCs), and human induced pluripotent stem cells (hiPSCs). FIG. 16B is a representative trace showing simultaneous acquisition of intracellular Ca2+(fura-2 fluorescence) and isometric twitch tension measured in an EHT containing hESC-derived cardiomyocytes. FIG. 16C is a representative twitch trace recorded in an EHT containing hiPSC-derived cardiomyocytes. The twitch is superimposed on a twitch produced by a human right ventricular trabecula. FIG. 16D shows mean twitch kinetic parameters and peak tension measured in hiPSC-EHTs (n=8). Gray bars indicate mean properties reported for human left ventricular muscle strips. Abbreviations: TTP, time to peak stress; RT50, time from peak to 50% relaxation.

FIG. 17A and FIG. 17B depict the results of histological analysis of cell distribution in a scaffold. All results were obtained from NRVMs seeded into laser-cut decellularized porcine myocardium at day 16. Scale bars are 50 FIG. 17A shows immunofluorescent staining for actin filaments (phalloidin, red) and nuclei (DAPI, blue). Inset shows magnification illustrating striated actin structure. FIG. 17B shows Masson's-trichrome Stain of longitudinally cut EHT. Nuclei (dark brown/black) are evenly distributed.

FIG. 18A and FIG. 18B depict the results of experiments demonstrating physiological function in laser-cut EHTs. All results were obtained from NRVMs seeded into laser-cut decellularized porcine myocardium. FIG. 18A shows the force-length relationship for peak tension and twitch kinetics (time to peak and relaxation time 50) of EHTs cultured for 9 (blue, n=11), 16 (grey, n=8), and 23 days (black, n=12), culture length of EHTs are 6 mm meaning that a stretch position of 0.6 mm represents 10% stretch. FIG. 18B shows the force-frequency relationship for peak tension and twitch kinetics at 8% stretch.

FIG. 20A through FIG. 20D depict the results of a scaffold comparison study using NRVM cells. Anisotropic electrospun gelatin scaffolds were compared with laser-cut decellularized myocardium. FIG. 20A is an SEM image showing the anisotropic fibers of the electrospun scaffold, Scale bar is 25 FIG. 20B illustrates the determinations of fiber alignment using Fast-Fourier-Transform and image processing tools within Matlab data analysis software. FIG. 20C illustrates that day 9 post-seeding, laser-cut decellularized myocardium (black, n=6) and anisotropic electrospun gelatin scaffolds (blue, n=7) exhibited a positive Frank-Starling response. FIG. 20D shows measurements of peak stress, time to peak (TTP) and relaxation time (RT50) in both scaffold types (Paired Student's t-test, *p<0.01)

FIG. 21A and FIG. 21B depict the results of experiments demonstrating lusitropic behavior of hiPSC-CM EHTs upon β-adrenergic agonist treatment. FIG. 21A shows representative traces of one 16 days old EHT at baseline and after treatment with 100 nM Isoproterenol. FIG. 21B shows mean twitch kinetic parameters and peak tension measured in hiPSC-EHTs (n=8) at baseline and after treatment with 100 nM of Isoproterenol (Paired Student's t-test, *p<0.05, **p<0.001).

FIG. 22A through FIG. 22C depict the results of experiments evaluating the pluripotency of iPSC. FIG. 22A shows stains for AFP (Endoderm), Desmin (Mesoderm), Nestin (Ectoderm) scale bar is 50 μm. FIG. 22B shows hiPSC line derived from a healthy control subject showing pluripotency markers. FIG. 22C shows normal karyotype for the derived hiPSC line.

FIG. 23 is a table depicting detailed fold change values of BNP up or down-regulation upon applied stretch or shear (in comparison to control). Expressions were normalized to GAPDH. Each batch of seeded tissues was analyzed within itself.

FIG. 24 depicts sequence ID numbers 1 through 6 for GAPDH, BNP, and ANP forward and reverse primers used in PCR analysis.

DETAILED DESCRIPTION

Figure 3:
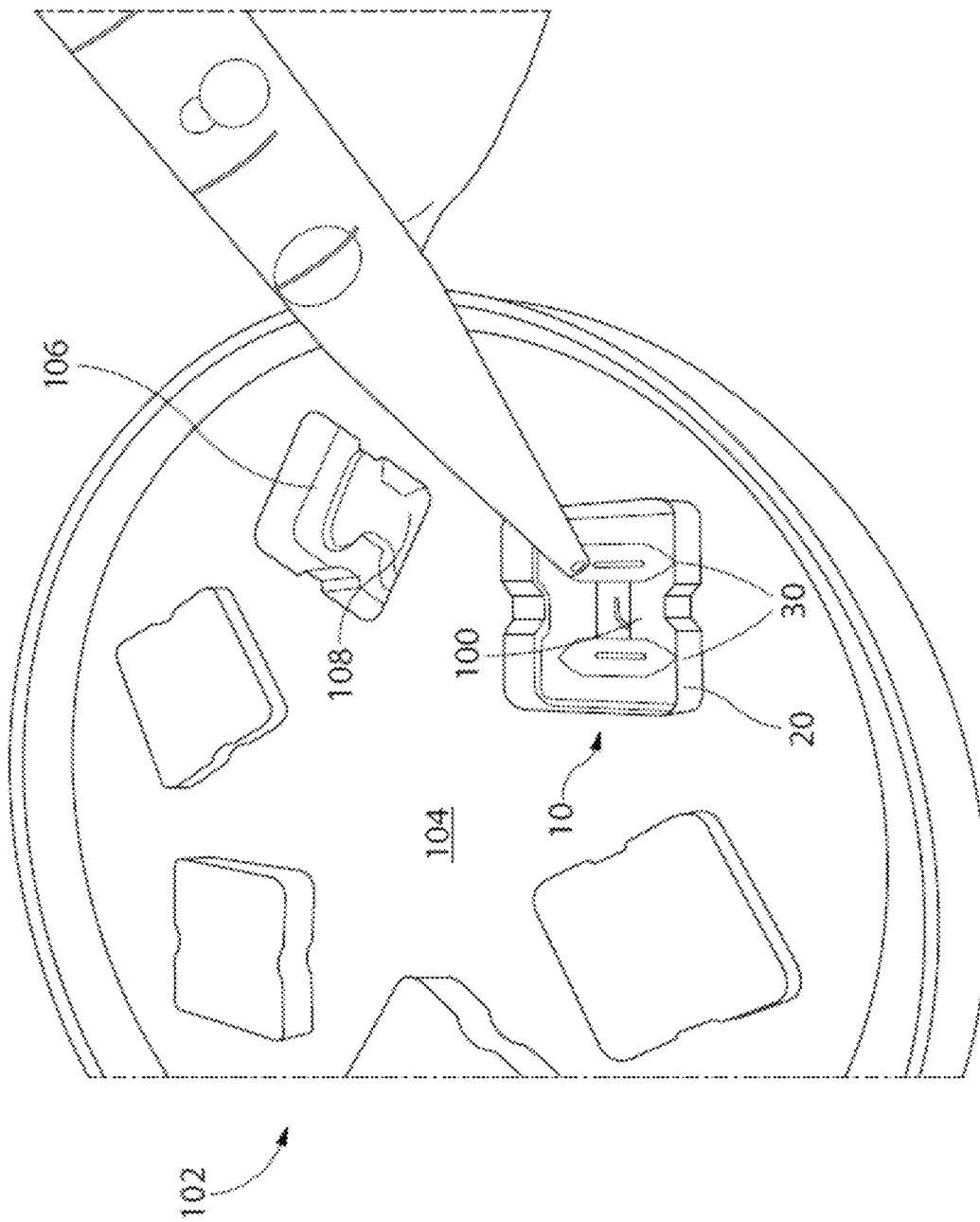
FIG. 3 depicts an exemplary cell seeding bath adapted for the tissue culture cassettes.

The present invention relates in part to devices, systems, and methods for the production and characterization of engineered tissue constructs. The devices and methods generate decellularized tissue constructs that can be recellularized using donor cells for high-throughput studies of organ physiology, and/or organ pathology. The devices and methods can be used with the systems to mechanically and electrically stimulate the engineered tissue constructs under culture or physiological conditions to detect and assess the presence and degree of any organ pathologies.

Definitions

Unless defined otherwise, all technical and scientific terms used herein have the same meaning as commonly understood by one of ordinary skill in the art. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, or ±5%, or 1%, or ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions, methods, and kits for the production of engineered tissue from patient-derived progenitor cells seeded onto decellularized laser-cut tissue constructs subjected to mechanical loading in an apparatus for such. Subsequent differentiated, engineered tissue can then be used for phenotypic screening for pathologies, for example cardiomyopathies, using tissue more faithfully representing donor tissue, for example cardiac tissue.

Scaffold Cassettes

The present invention provides in part cassettes for mounting tissue constructs. The cassettes are capable of suspending a tissue construct for culturing and for mechanical testing. Referring now to FIG. 1A through FIG. 1B, an exemplary cassette 10 is depicted. Cassette 10 comprises a frame 20, at least two clips 30, and at least two tabs 40 for securing a tissue scaffold 100. Frame 20 comprises at least two clip slots 12, each clip slot 12 sized to fit a clip 30. Each clip 30 comprises an elongated shape having a central slit 32. Clip 30 can have any suitable shape, including rectangular and hexagonal prism shapes. Clip 30 can have any suitable dimensions. For example, clip 30 can have a length between about 5 mm and 15 mm, a width between about 1 mm and 4 mm, and a height between about 1 mm and 4 mm.

Referring now to FIG. 2A through FIG. 2F, exemplary tabs 40 are depicted. Tabs 40 are generally sized to fit within the central slit 32 of each clip 30. Tab 40 can have any suitable size, such as a length between about 3 mm and 5 mm, a width between about 1 mm and 2 mm, and a height between about 0.25 mm and 1 mm. In some embodiments, tab 40 comprises a core 42 with an outer layer of expandable material 44 (FIG. 2A). Core 42 has an elongate shape and can have any suitable cross-section, including but not limited to circular cross-sections, ovoid cross-sections, square cross-sections, rectangular cross-sections, and the like. Core 42 can have any suitable size, including a length between about 2 and 5 mm and a width between about 0.5 and 2 mm.

Expandable material 44 is capable of retaining a first size and a second size to decrease and/or increase the cross-sectional area of tab 40. In some embodiments, expandable material 44 can be a compressible material, such as a foam material, wherein the material can receive a compressive force to be compressed from a larger first size to a smaller second size, and removal of the compressive force causes the material to return to the first size. In other embodiments, expandable material 44 can be a dry or partially dry material having a smaller first size and can swell into a larger second size after absorbing a fluid. In various embodiments, the fluid can be culture media, isotonic saline solution, buffered saline solution such as phosphate-buffered saline solution, reductionist media, or basal media.

Tab 40 having an outer layer of expandable material 44 is able to gently secure a scaffold 100 in place by locking a length of scaffold 100 into slit 32 of clip 30. For example, as illustrated in progressive FIG. 2B and FIG. 2C, a compacted tab 40 can fit within slit 32 with room around tab 40 to wrap a length of scaffold 100. The expansion of expandable material 44, such as by swelling after contact with an aqueous solution or by returning to an uncompressed size, increases the cross-sectional area of tab 40 in at least one dimension to gently and securely lock scaffold 100 to clip 30 by way of friction between tab 40, scaffold 100 and walls of slit 32 in clip 30. In some embodiments, tab 40 is constructed entirely from expandable material 44, such as in FIG. 2D through FIG. 2F, and is able to gently secure a scaffold 100 using the same principle as described above. Tab 40 is able to secure scaffold 100 into clip 30 while retaining tissue integrity, allowing the excised tissue sample to remain intact and secured for mechanical loading.

Referring now to FIG. 3, an exemplary cell-seeding bath 102 compatible with the cassettes 10 of the present invention is depicted. Cell-seeding bath 102 comprises a substrate 104 having a top surface with one or more well 106 embedded within the top surface. Each well 106 comprises a shape sized to fit a frame 20 of the cassettes 10 of the present invention. At the bottom of each well 106, an indent 108 is provided, wherein indent 108 is sized to fit a section of a tissue scaffold suspended between two clips 30.

Figure 4A:
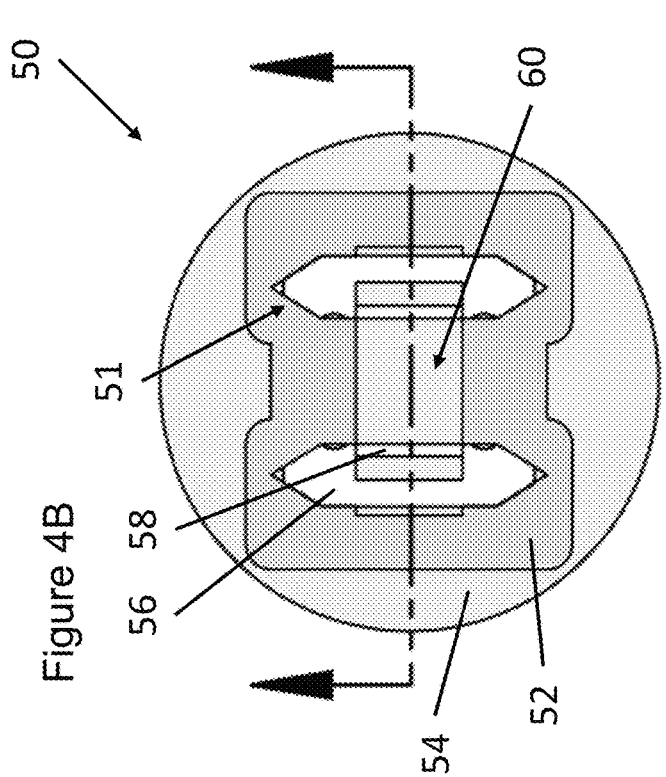
FIG. 4A through FIG. 4C depict an exemplary cassette adapted for generating hydrogel-based constructs.
Figure 4B:
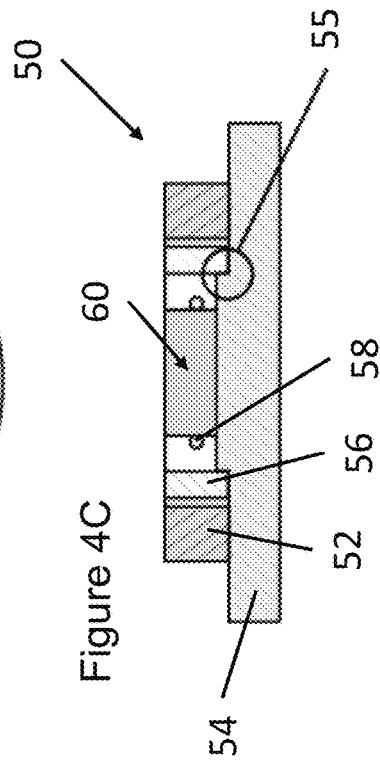
Figure 4C:
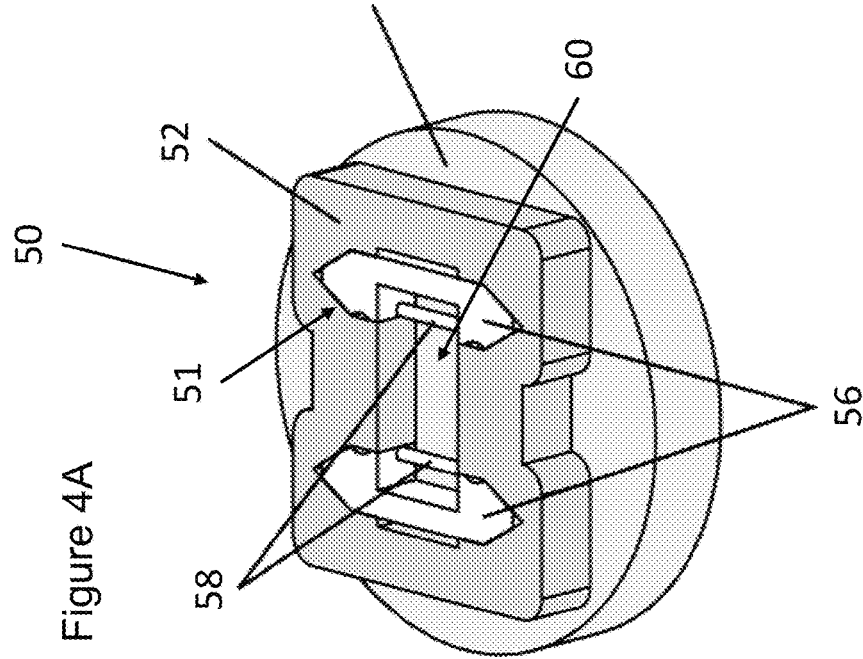

Referring now to FIG. 4A through FIG. 4C, another exemplary cassette 50 is depicted. Cassette 50 can be used without any tabs and comprises frame 52, pedestal 54, and at least two clips 56. Frame 52 comprises a centrally positioned mold space 60 and at least two clip slots 51 positioned at opposite ends of mold space 60, each clip slot 51 sized to fit a clip 56. Each clip 56 comprises an elongated shape having a laterally facing opening with bar 58 suspended within the laterally facing opening. Inserting the at least two clips 56 into clip slots 51 positions the laterally facing openings towards mold space 60, thereby capping mold space 60 at opposite ends with a clip 56 and a bar 58. Clip 56 can have any suitable shape, including rectangular and hexagonal prism shapes. Clip 56 can have any suitable dimensions. For example, clip 56 can have a length between about 5 mm and 15 mm, a width between about 1 mm and 4 mm, and a height between about 1 mm and 4 mm. Pedestal 54 is a solid structure having a substantially flat upper surface with a raised surface 55 having the same surface area as mold space 60. Frame 52 and the at least two clips 56 can be seated on top of pedestal 54 such that raised surface 55 seals off the bottom of mold space 60. In certain embodiments, frame 52 and pedestal 54 can be constructed as a single unit.

The various components of the scaffold cassettes of the present invention can be made from any suitable material. For example, the frames, clips, tab cores, cell-seeding baths, and pedestals described above can be constructed from a polymer, a plastic, a metal, or a glass. In some embodiments, the scaffold cassettes are at least partially constructed from polydimethylsiloxane (PDMS), which may be prepared by mixing an elastomer and a curing agent at a ratio of 1:10. In some embodiments, the scaffold cassettes are at least partially constructed from polytetrafluoroethylene (PTFE).

In some embodiments, expandable materials can include hydrogels. Hydrogels can comprise any biopolymer or synthetic polymer known in the art. For example, the hydrogel may comprise hyaluronans, chitosans, alginates, collagen, dextran, pectin, carrageenan, polylysine, gelatin, or agarose. (see.: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12).

The scaffold cassettes can be made using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the components may be made using 3D printing or other additive manufacturing techniques commonly used in the art.

Tissue Sample Scaffolds

The scaffold cassettes of the present invention can be used to hold one or more tissue samples and scaffolds for culturing and mechanical testing. In some embodiments, the tissue samples of the invention are derived in part from organs of large animals, including but not limited to pigs and humans. The organs can be any desired organ, including liver, lung, kidney, spleen, skin, heart, striated muscle, smooth muscle, tendons, ligaments, and the like. In some embodiments, the tissue samples include decellularized constructs, including decellularized cardiac samples.

Figure 5A:
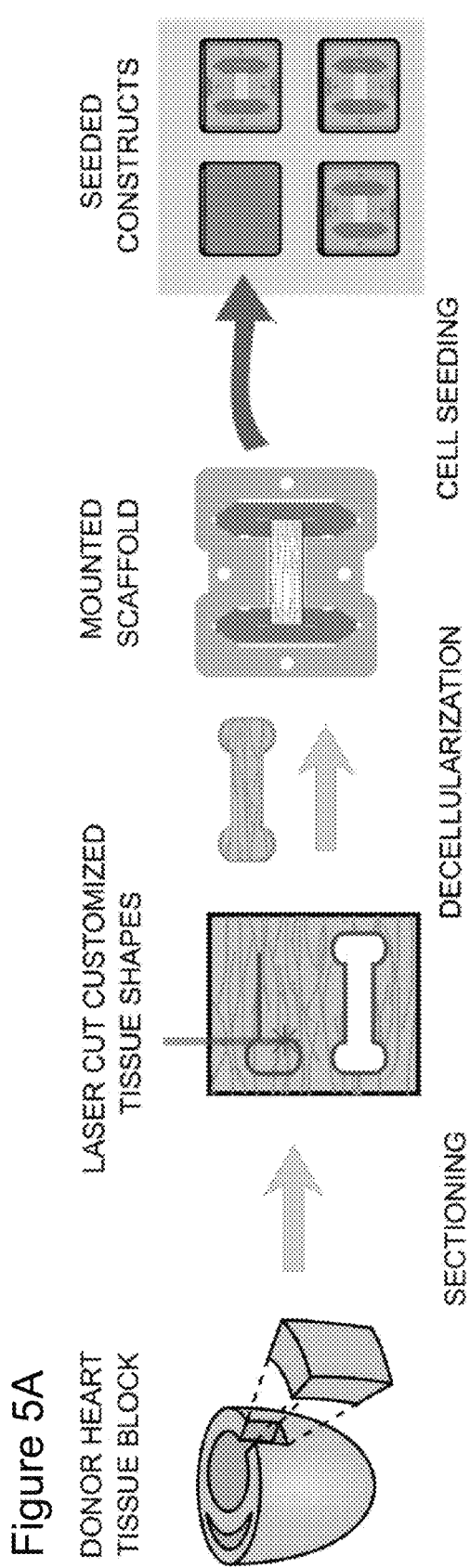
FIG. 5A through FIG. 5E depict the steps in scaffold generation.

Referring now to FIG. 5A, an exemplary method of forming engineered heart tissue (EHT) compatible with the scaffold cassettes of the present invention is depicted. The first step excises a cardiac tissue sample from a heart. Cardiac tissue samples can be excised from any part of the heart, including the ventricular wall. In one embodiment, the cardiac tissue samples are excised from the left ventricular free-wall (non-septum wall) of donor hearts. The excised tissue samples are cut into sheets. In one embodiment, the tissue samples are cryosectioned into sheets having thicknesses between about 100 µm and 200 µm. Tissue shapes compatible with the scaffold cassettes of the present invention are cut from the tissue sheets. In one embodiment, the tissue sheets are precision cut using a cutting device, such as a laser. The tissue shapes can have any suitable size and shape, such as a dog bone shape having a width of about 5 mm and a length of about 6 mm. In some embodiments, the tissue sheet construct is cut such that the tissue fibers in the resulting tissue shape are oriented parallel to the long axis of the precision cut shape in such a manner that native tissue anisotropy is retained. In certain embodiments, the tissue shapes can be created from any suitable scaffold. The scaffolds can be molded into the dimensions of a desired tissue shape, or precision cut from an electrospun or woven scaffold sheet.

The tissue shapes are amenable to any suitable treatment before or after mounting onto a scaffold cassette. For example, the tissue shapes can be treated with a decellularization step to yield an acellular tissue scaffold. The tissue samples may be decellularized by bringing the tissue samples into contact with a decellularizing solution. For example, a tissue sample may be brought into contact with a decellularizing solution in a manner including but not limited to entirely submerging, partially submerging, coating with, and incubating with a decellularizing solution. In one embodiment, the reagent or solution comprises an ionic detergent, including but not limited to sodium deoxycholate (SDC), sodium dodecyl sulfate (SDS), Triton X-200, and the like. In one embodiment, the reagent or solution comprises a non-ionic detergent, including but not limited to Triton X-100, Triton X-114, and the like. In one embodiment, the reagent or solution comprises an acidic or a basic solution, including but not limited to paracetic acid. In one embodiment, the reagent or solution comprises a hypotonic or hypertonic solution which lyses cells by osmotic pressure. In one embodiment, the reagent or solution comprises a zwitterionic solution, including but not limited to CHAPS, Sulfobetaine-10 and -16, and the like. In one embodiment, the reagent or solution comprises a solvent, including but not limited to alcohols, acetone, or tributyle phosphate. In one embodiment, the reagent or solution comprises enzymes which degrade cellular components or other biomolecules. In certain embodiments, the reagent or solution comprises an enzyme activating element, such as magnesium or calcium. Such enzymes include but are not limited to trypsin, DNase, RNase, dipase, and the like. In one embodiment, the reagent or solutions may be combined with a physical or mechanical method, including but not limited to freezing and thawing, electrical stimulation, physical force, perfusion, sonication, or agitation.

In various embodiments, the tissue shapes can be treated with a cell-seeding step to yield a seeded construct. As described above, the present invention provides in part cell-seeding baths 102 shown in FIG. 3. FIG. 3 further depicts a cassette 10 having a scaffold 100 attached to two clips 30 in a frame 20, wherein the cassette 10 is inverted within a well 106 such that the scaffold 100 and the two clips 30 are seated within indent 108. In this configuration, a cell-laden solution may be deposited within well 106, permitting the cells to settle onto scaffold 100.

The cells can be any suitable cell, including progenitor cells, pluripotent cells, stem cells, other differentiable cells, and the like. The differentiable cells can be described by way of their origin, such as embryonic stems cells, hematopoietic stem cells, adipose derived stem cells, bone marrow derived stem cells and the like. In some embodiments, the differentiable cells are directed to differentiate into cells of target tissues, for example fibroblasts, osteocytes, epithelial cells, endothelial cells, myocytes, neurocytes, and the like.

While the description of the invention is exemplified for the production of decellularized heart constructs, a skilled artisan would recognize that the present invention is not limited to the heart tissue. Rather, the compositions, methods, and kits of the present invention are suitable for the decellularization and/or recellularization of any biological tissue or organ, in particular those subjected to mechanical loading in their native microenvironment.

In one embodiment, the present invention provides for the production of small decellularized tissue constructs for use in high-throughput studies. In one embodiment, the decellularized constructs of the invention retain three-dimensional structure. These small decellularized constructs may be used, for example, in studies examining the effects of mechanical, pharmacological, biochemical, and environmental conditions on tissue decellularization and/or recellularization. In certain embodiments, the constructs are small decellularized tissue constructs. In one embodiment, the decellularized tissue constructs are capable of being ventilated and perfused.

Referring now to FIG. 6A through FIG. 6C, an exemplary method of forming a hydrogel-based construct using a scaffold cassette of the present invention is depicted. In FIG. 6A, an amount of a hydrogel loaded with at least one cell is placed within a mold cavity formed by a cassette, at least two clips, and a pedestal. After incubating the cells within the hydrogel for a period of time, the amount of hydrogel becomes compacted around the bars of each clip to form a hydrogel-based construct, as shown in FIG. 6B. The hydrogel-based construct may then be removed with the clips for use in any desired experiment or study, as shown in FIG. 6C.

Bioreactor System

The scaffold cassettes of the present invention can be used with a bioreactor system to conduct mechanical testing of tissue scaffold samples under various conditions. Referring now to FIG. 7A and FIG. 7B, an exemplary bioreactor system 200 is depicted with clips from a scaffold cassette attached. Bioreactor system comprises actuator 202 connected to a first clip by arm 204, force measuring component 300 connected to a second clip by arm 302, and electrode component 400 positioned within a reservoir 206 below the first clip and the second clip. The connection between the arms and clips can be achieved using any suitable means, such as using clamps, tabs, hooks, slots, and the like.

Figure 8A:
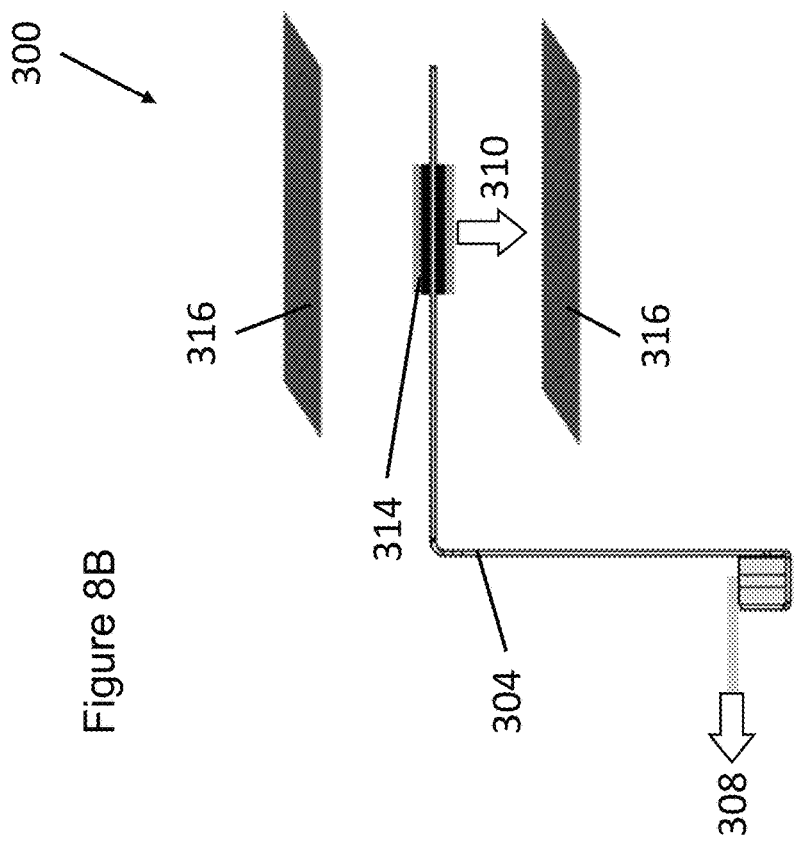
FIG. 8A and FIG. 8B depict an exemplary force measuring device.
Figure 8B:
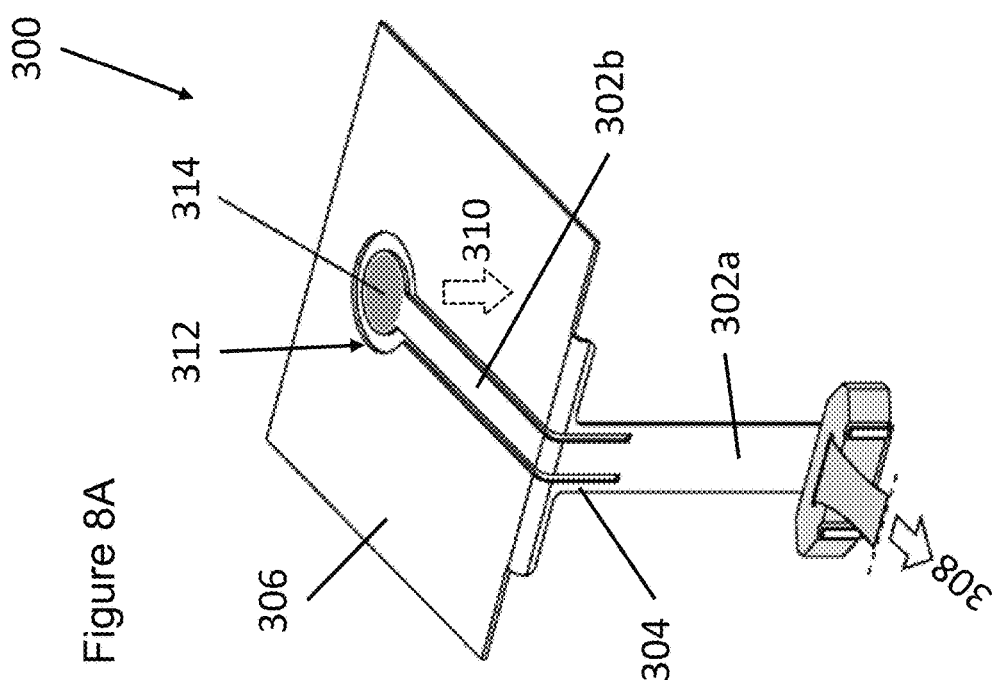

Referring now to FIG. 8A and FIG. 8B, force measuring component 300 is described in detail. Force measuring component 300 comprises arm 302 having arm segment 302a and arm segment 302b. Arm segment 302a is joined to a planar plate 306 at fitting 304. Fitting 304 is a solid connection that permits non-deformable bending between arm segment 302a and plate 306, such that shifting arm segment 302a bends arm segment 302a relative to plate 306 but does not bend arm segment 302a relative to arm segment 302b. For example, applying tension to arm segment 302a in direction 308 causes arm segment 302a to bend relative to an immobile plate 306, while arm segment 302b, not bound to plate 306, shifts in direction 310 due to its connection with arm segment 302a. Plate 306 has a cutout 312 sized to permit arm segment 302b to move in-plane and out-of-plane with plate 306. Arm segment 302b comprises at least one conductive target 310. Visible in FIG. 8B, plate 306 comprises one or more sensors 316 positioned above conductive target 310, below conductive target 310, or both. As arm segment 302b moves out-of-plane with plate 306 in response to a shifting arm segment 302a, the position of conductive target 310 changes relative to the at least one sensor 316. The displacement in conductive target 310 can thereby be detected by the at least one sensor 316 and used to calculate the magnitude of the force shifting arm segment 302a.

Figure 9:
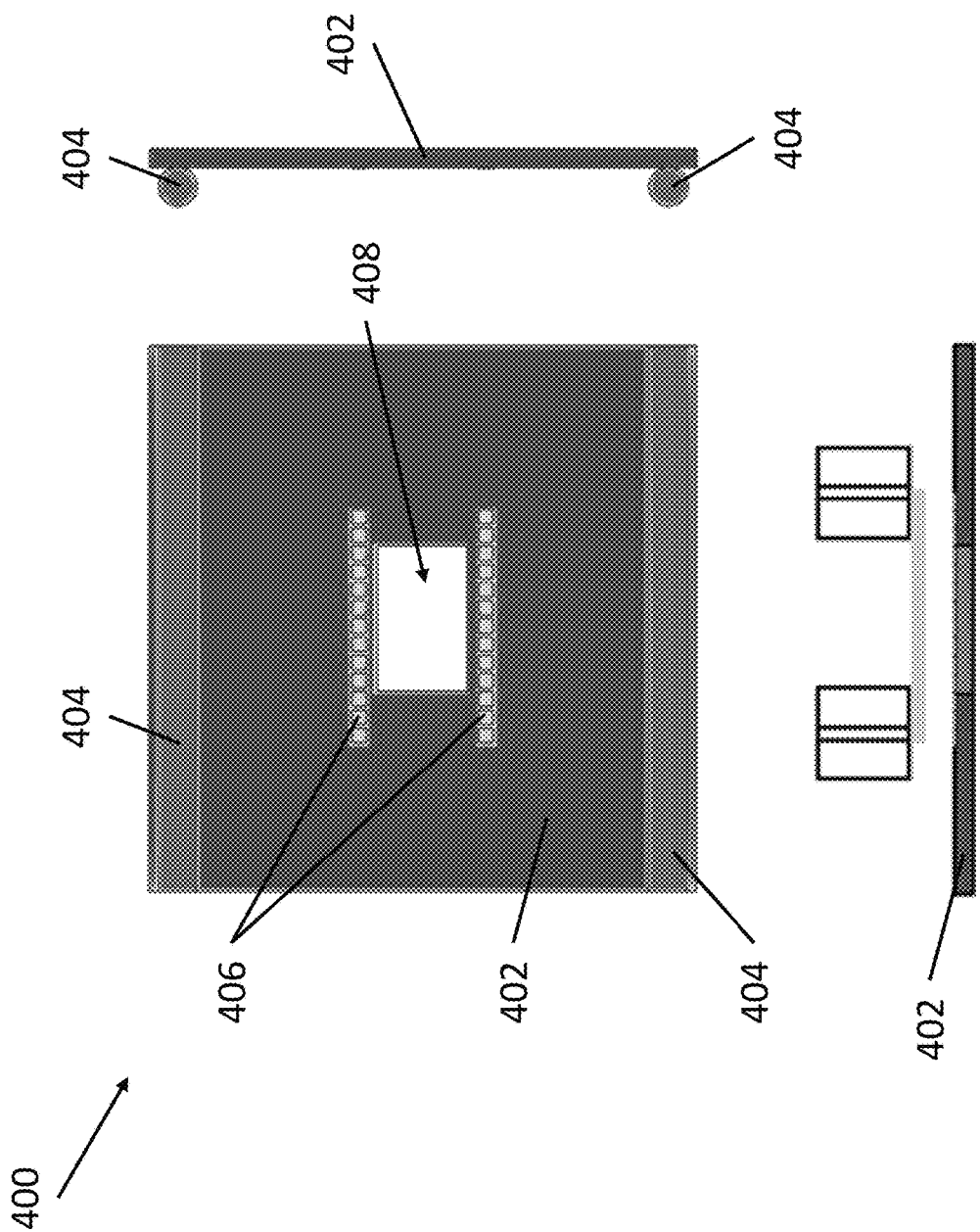
FIG. 9 depicts a top-down view, a side view, and a cross-sectional view of a circuit board assembly of the bioreactor depicted in FIG. 7A and FIG. 7B.

As described above, electrode component 400 is positioned within reservoir 206 underneath a first and second clip connected to bioreactor system 200. Reservoir 206 can be filled with an aqueous solution to submerge electrode component 400, the first clip, the second clip, and a tissue scaffold sample suspended between the first and second clips. Selective activation of electrode component 400 conducts electricity through the aqueous solution, which generates an electrical field across regions of reservoir 206 to stimulate a submerged tissue scaffold sample. Referring now to FIG. 9, electrode component 400 is described in detail. Electrode component 400 comprises circuit board 402, at least two electrodes 404, and electrode array 406. In some embodiments, circuit board 402 comprises a centrally positioned window 408 to permit imaging of a suspended tissue scaffold sample. The at least two electrodes 404 are elongate electrodes positioned in parallel along opposite edges of circuit board 402. The at least two electrodes 404 are thereby configured to generate a substantially uniform electric field across circuit board 402. Electrode array 406 comprises a plurality of electrodes positioned near the center of circuit board 402, such that a submerged tissue scaffold sample is at least partially above electrode array 406. Electrode array 406 can have any number of electrodes arranged in any suitable pattern, including but not limited to 1, 2, 3, 4, 5, 6, 8, 10, 12, 15, 20, 25, 30, or more electrodes in a grid or parallel linear arrangements. Electrode array 406 is configured to measure the extracellular potential of a region of a submerged tissue scaffold sample directly above each electrode. The measurements from each electrode may be combined to generate an activation map of the submerged tissue scaffold sample and can be used to calculate the speed of signal propagation through the sample. In some embodiments, arm 204 and arm 302 each comprise at least one electrode near their connections to the first clip and the second clip, respectively, wherein the electrodes are configured to provide a localized electrical stimulus to a submerged tissue scaffold sample.

Phenotypic Screening

The scaffold cassette devices and bioreactor systems of the present invention can be useful in screening for phenotypic markers in engineered heart tissue (EHT). ETHs can be constructed using tissue from a patient, and the EHT containing the patient's tissue can be maintained on a scaffold cassette and mechanically tested in a bioreactor system to screen for any diseases or disorders, including cardiomyopathies. The cardiomyopathies can include: hypertrophic cardiomyopathy, dilated cardiomyopathy, restrictive cardiomyopathy, arrhythmogenic right ventricular dysplasia, and unclassified cardiomyopathy. In one embodiment, the engineered tissue is assayed to identify phenotypic markers in tissue engineered from cells collected from donors with a known cardiomyopathy.

Figure 10:
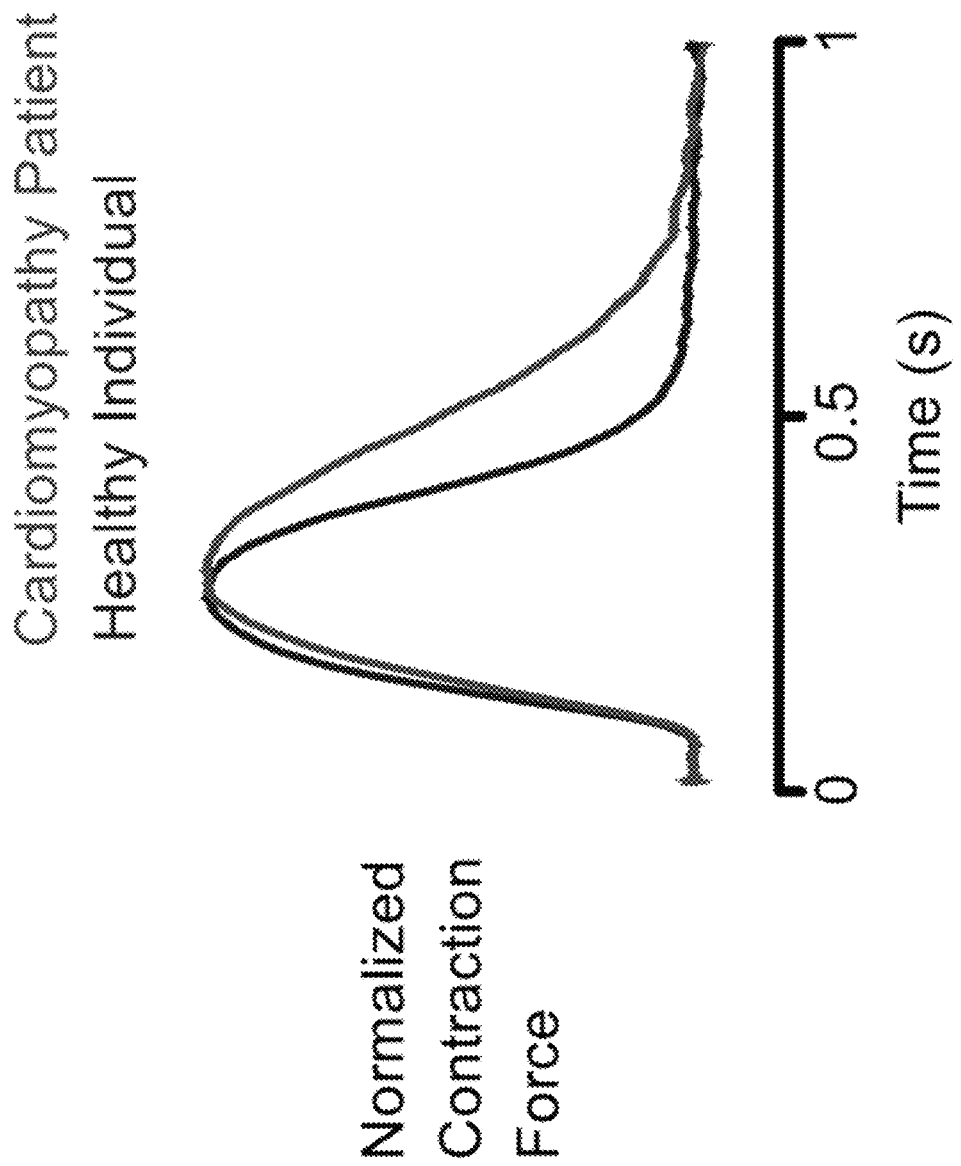
FIG. 10 depicts the results of experiments demonstrating the use of EHT to identify intrinsic cardia abnormalities. EHT were formed from induced pluripotent stem cell lines obtained from a healthy individual and a cardiomyopathy patient. Twitch contraction force was measured in both tissue types. The tissue developed from the cardiomyopathy patient manifest a highly significant difference in rate of force relaxation. The parameters defining the shape of twitch contraction time course, in addition to the twitch amplitude, reveal intrinsic differences between healthy and diseased individuals.

Referring now to FIG. 10, the results of an exemplary phenotypic screen between a cardiomyopathy patient and a healthy patient are shown. Induced pluripotent cells were collected from each of the cardiomyopathy patient and the healthy patient. The cells were successful cultured in scaffolds to form EHTs adapted for use with the scaffold cassettes of the present invention, each EHT having cells from either the cardiomyopathy patient or the healthy patient. The EHTs were removed from the scaffold cassettes using the attached clips and loaded into a bioreactor system, wherein twitch contraction force was measured in the EHTs by electrically stimulating the EHTs and recording measurements using a force measuring component. The results show that the EHT formed from the cells of the healthy patient has a uniform rate in twitch contraction and relaxation, while the EHT formed from the cells of the cardiomyopathy patient shows a deviation in relaxation rate.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1: Laser-Cut Myocardium as a Source of Anisotropic Scaffolding for Cardiac Tissue Engineering Abnormal growth and remodeling of the myocardium are central features in many heart disorders, including hypertensive heart disease, myocardial infarction, and inherited cardiomyopathies. Such phenomena are challenging to study because of the many different factors that can perturb cardiac tissue homeostasis in vivo. These can include gene mutations, endocrine factors, and mechanical loads applied to the tissue. Engineered heart tissues (EHTs) could be transformative in vitro tools for studying the remodeling process, because they allow the various contributing factors to be manipulated systematically in a controlled environment.

In order to be most useful for cardiac remodeling studies, EHTs should have an extracellular matrix (ECM) with realistic molecular composition and three-dimensional microstructure. Cardiac cells sense their mechanical environment through structures that link the cytoskeleton to specific ECM components. Therefore, an ECM composition that provides the proper set of binding partners for cells could be a critical factor in recapitulating in vivo mechanical signaling. Besides composition, the microstructural arrangement of ECM proteins is likely to be a key consideration. In healthy myocardium, cardiomyocytes are aligned to form a local prevailing fiber direction. The passive and active material properties of the myocardium depend strongly on whether they are measured parallel or perpendicular to these fibers. That is to say, the myocardium is highly anisotropic. This suggests that mechanosensitive responses in cardiac tissue should also be studied in the context of carefully controlled material anisotropy.

Decellularized adult myocardium is a scaffold that provides realistic anisotropy and matrix composition. It is produced by treating tissue with chemicals that remove intracellular contents, leaving only the native extracellular matrix behind. Ott et al. used this pioneering approach to produce functioning cardiac tissue by seeding neonatal rat ventricular myocytes (NRVMs) as well as human induced pluripotent stem cell-derived cardiomyocytes (hiPSC-CM) into perfusion-decellularized hearts. Lu et al. later demonstrated the ability of decellularized mouse myocardium to promote differentiation and assembly of human cardiovascular progenitor cells into viable cardiac tissue. More recently, thick slices of decellularized myocardium have been immobilized on cover glass and seeded with NRVMs to produce tissue sheets with anisotropic action potential conduction. These studies and others highlight the clear potential of decellularized myocardium to produce cardiac tissues with realistic anisotropy, but until now this technology has not been adapted for biomechanical experiments, which require the ability to both measure and manipulate mechanical loading of EHTs in precise ways.

Figure 5B:
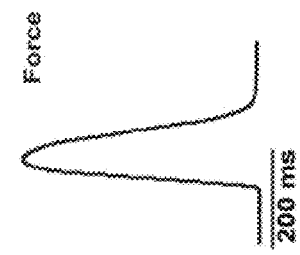

The present study reports two key advances that fully harness the potential of decellularized myocardium. After cutting thin cryosections of adult porcine myocardium, laser cutting was successfully used to generate scaffolds with customizable, engineered shapes (FIG. 5A). An innovative clipping system has also been developed that mounts the ribbon-like scaffolds consistently and securely into a tissue culture 'cassette' (FIG. 5B). Scaffolds are then decellularized and reseeded with human or rat cardiac cells, ultimately yielding robust EHTs that are well suited for several biomechanical assays. The process of laser cutting allows us to precisely orient cardiac fibers relative to the macroscopic dimensions of the final construct. The clipping system enables precise application of novel mechanical perturbations (such as shear strain) and makes measurements of mechanical function rapid and reliable.

Methods

Tissue Culture Cassette

An in vitro culturing system was designed that protects the tissue during decellularization, allows the application of precise mechanical boundary conditions, facilitates repetitive, non-damaging transfer between culture and biomechanical testing apparatus, and allows for straightforward force measurements. The final tissue culture cassette design consists of two clips that mount into a frame as depicted in FIG. 5B. This ensures that the scaffold is held securely at a constant length throughout seeding and culture. Tissue culture cassettes were cut out of Polytetrafluoroethylene (PTFE), which allowed them to be biocompatible, autoclavable, and reusable.

Generation of Thin Myocardial Slices

Blocks of myocardium were dissected from the left ventricular free walls of young porcine hearts and flash frozen in powdered dry ice. Slices (150 μm-thick) were cut from each tissue block using a cryostat microtome. Blocks were oriented so that the cutting face was roughly parallel to the epicardial surface, ensuring that native cardiac fibers lay in the section plane. Sections were always taken from the mid-myocardium, since mechanical properties of the tissue at different wall depths are known to vary significantly. Cut slices were stored at −80° C. for up to two months.

Generation of Customized Shapes Using Laser Cutting

Thin myocardial sheets were mounted on glass cover slips, thawed, and placed inside an infrared laser cutter to generate precise computer-designed shapes. Scaffolds could be rotated prior to cutting in order to control the orientation of the naturally occurring tissue fibers relative to the designed shape. In typical experiments, the sheets were rotated such that the fibers were oriented parallel to the longitudinal axis of the cut pattern. A commercial 35-watt $CO_2$ laser cutter was used to cut tissues into computer-designed shapes. Outlines were traced twice with 25% power and 100% speed to complete the full cut. The central portion of the scaffold, where cells were ultimately deposited, was a rectangular dog-bone shape of 5 mm wide and 6 mm long (FIG. 11A).

Decellularization

Figure 5C:
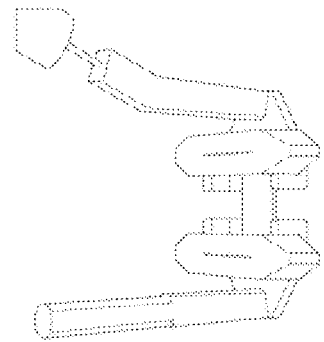

To protect the tissue during decellularization steps, it was temporarily mounted onto removable posts positioned in the culture frame (visible in FIG. 11B). Endogenous cellular contents of the pig myocardium were then removed through a decellularization procedure as described previously, with some modifications (FIG. 11C). After decellularization, each end of the scaffold was secured to a clip in the tissue culture cassette by wedging the ends of the decellularized myocardium into a narrow slit located at the clip's center (FIG. 5C). The tissue was mounted into the slit by a thin rectangular tab made of polyester sheeting. Friction between the tab and the sides of the slit kept the scaffold gently but securely clamped throughout the culture period and during mechanical testing. The frame ensured that clips were held at a specified length during culture. All incubations were performed at room temperature unless stated otherwise. In brief, the tissues were incubated in a cell lysis buffer (10 mM Tris, 0.1% wt/vol EDTA, pH 7.4) for 2 hours followed by a 40-minute incubation in sodium dodecyl sulfate (0.5% wt/vol in PBS) with gentle agitation (35 rpm on an incubated shaker). Tissues were washed three times in PBS and incubated in DMEM containing 10% FBS for 24 hours at 37° C. to remove residual DNA1. Sterilization was performed by placing the tissues in 0.1% peracetic acid and 4% ethanol for 5 minutes. Tissues were washed three times in PBS before being attached to PTFE clips for seeding and culture Cell Derivation/Preparation of Cardiomyocytes The neonatal rat ventricular myocytes (NRVMs) used in most experiments were obtained using standard methods. H9 human embryonic stem cells (hESCs) (Bartulos, O. et al. JCI Insight, 2016, 1:1-17, Wang, Y. et al. Circ Res, 2012, 111: 1494-1503) were also used in some tests. To assess the ability of the constructs described herein to characterize patient-derived cardiomyocytes, a new induced pluripotent stem cell (hiPSC) line was created from a healthy human donor using a method previously reported.

Neonatal Rat Ventricular Myocytes (NRVM)

NRVMs were isolated from 1-3 day old Sprague Dawley rat pups using a standard protocol (McCain, M. L. & Parker, K. K. Pflugers Arch—Eur J Physiol, 2011, 462:89-104). In brief, hearts were dissected, minced, and digested using a solution containing Type II collagenase (0.5 mg/ml, Worthington Biochemical Corporation) and protease (0.1 mg/ml, Sigma Aldrich). During constant rotational digestion, cell suspensions were collected in batches every 20-30 minutes. Each aliquot was spun by gentle centrifugation and pre-plated for 90 minutes on standard cell-culture plates in DMEM containing 10% FBS and Pen/Strep. The remaining cell suspension of cardiomyocytes, considered fibroblast-depleted, was collected from the pre-plating culture plates, combined into a single aliquot, spun down and resuspended in complete culture media for seeding into EHTs. One million cells were seeded per decellularized scaffold.

Human Embryonic Stem Cell (hESC) Culture and Cardiac Differentiation hESC from the hESC line H93 were cultured with mTeSR (Stemcell Technologies) on reduced growth factor—Matrigel (BD Falcon™)—coated plates until they reached 80-90% confluence. Cells were detached with 1 mg/ml Accutase (Innovative Cell Technologies) for 5 minutes and $5\times10^4$ cells/cm² were plated on Matrigel-coated 12-well plates in the presence of 5 µM of the inhibitor Y-27632 (Calbiochem), which was removed the following morning. Cells were maintained in mTeSR until they had 80-85% confluence (4 days). Differentiation to cardiomyocytes was performed as previously described[4]. Briefly, four days after plating, hESCs were cultured in B27/RPMI medium; RPMI 1640 (Life Technologies) with B27 minus insulin (Life Technologies), containing 10 µM CHIR99021 (Selleck Chemicals). Twenty-four hours later (day 1 of differentiation), the medium was replaced with fresh B27/RPMI medium. On day 3 of differentiation half of the medium was removed and the other half was mixed with fresh B27/RPMI medium and 5 µM of the Wnt Inhibitor IWP4 (Stemgent) was included in the solution. On day 5 of differentiation, the medium was replaced with fresh B27/RPMI medium. After day 5, medium was replaced every 3 days with fresh B27/RPMI medium. On day 14 of differentiation, cardiomyocytes were detached with 1 mg/ml Accutase for 10 minutes and a single cell suspension was obtained after application of mechanical force. Only batches with 45-75% cardiomyocytes were utilized for experiments (based on cardiac troponin T staining of a test aliquot). Spheroids were prepared with $1\times10^4$ cells per spheroid in 0.24% methylcellulose (Sigma-Aldrich) as previously described[5], with some modifications. Twenty-four hours after plating the cells on 96-U bottom low attachment plates, the vast majority of the cells were aggregated into spheroids. Spheroids were collected and washed 3 times with RPMI 1640. One million cells (~200 spheroids) were seeded per decellularized scaffold.

iPS Cell Derivation

Briefly, 10 ml of whole blood from a healthy, male donor was collected by venipuncture under the approval of Yale Institutional Review Board. Peripheral blood mononuclear cell (PBMCs) were isolated using a Ficoll-paque (GE healthcare) based method. PBMCs were cultured on anti-CD3 antibody (BD Biosciences) coated plate in 10% FBS RPMI-1640 medium with the addition 120 ng/ml of IL2 (BD Biosciences) for 5 days. To enable reprogramming of PBMCs to iPSC, PBMCs were infected with Sedai virus (CytoTune®-iPS Sendai Reprogramming Kits, Invitrogen) according to the manufactory instruction. The infected cells were seeded on irradiated mouse embryonic fibroblast cell covered plates for 3-4 weeks in human embryonic stem cells medium (20% Knock out Serum Replacement, 1% Glucose, 1% NEAA, 55 uM beta-mecaptoethanol in DMEM/F12 basal medium containing bFGF 10 ng/m1). The clones were then picked and expanded for differentiation after 15 passages to ensure removal of virus and stained for pluripotency markers OCT4, SSEA-4, NANOG, TRA-1-60, and alkaline phosphatase (FIG. 22B).

Cardiac Differentiation of iPSCs

Briefly, iPSCs were dissociated with dispase and gentle agitation and transferred to a 15 ml conical tube. After settling for 7 minutes, the supernatant was removed and the pellet resuspended in 2 ml mTeSR media (StemCell Technologies) and transferred to a Matrigel-coated plate (BD Biosciences). Cells were maintained in mTeSR media until they reached 90% confluency (4-5 days). Once confluency was reached, iPSCs were cultured in B27/RPMI medium containing 25 ng/ml CHIR99021 (Selleck Chemicals). Twenty-four hours later (day 1 of differentiation), the medium was replaced with fresh B27/RPMI medium. On day 3 of differentiation half of the medium was removed and the other half was mixed with fresh B27/RPMI medium and 5 µM of the Wnt Inhibitor IWP4 (Stemgent). On day 5 of differentiation, the medium was replaced with fresh B27/RPMI medium. After day 5, medium was replaced every 3 days with fresh B27/RPMI medium. Beating clusters were usually observed at day 8-9. At day 14, cells were subjected to dissociation.

Seeding of EHTs in PDMS Baths

Cellular seeding was performed in customized seeding baths that confined the cell suspension to a volume directly surrounding the mounted scaffold. Scaffolds were placed face-down to increase seeding efficiency and reduce overall seeding volume (FIG. 3). Seeding baths were made out of polydimethylsiloxane (PDMS). Elastomer and curing agent were mixed at a ratio of 10:1, poured into a 3D printed mold, and baked at 60° C. for 8 h. Exact seeding conditions differed slightly with altered media conditions for NRVMs, hESC-CMs and hiPSC-CMs. For NRVMs/hESC-CMs individual decellularized scaffolds were seeded with 100 µL cell suspensions containing 10 million cells/ml (~1 M cells of either NRVMs, hESC-CMs/EHT). After 2 hours, 1 ml of NRVM/hESC-CM culture media consisting of high glucose DMEM with 10% horse serum, 2% FBS, 10 µg/mL insulin, 50 µg/mL ascorbic acid and 1% of antibiotic-antimycotic solution was added. Unless stated otherwise, the antibiotic-antimycotic solution was only used for the first 24 hours and removed thereafter to minimize the impact of streptomycin on stretch-activated ion channels and prevent toxicity20. Constructs seeded with NRVMs were treated with 100 µM bromodeoxyuridine for the first 48 hours to reduce non-cardiomyocyte cell growth. EHTs seeded with iPSC-CM were also seeded with 100 µL cell suspensions containing 10 million cells/ml in seeding media (D-MEM (high glucose), 10% fetal bovine serum (FBS), 0.1 mM MEM Non-Essential Amino Acids, 2 mM L-glutamine, 5 µM of the inhibitor Y-27632 (Calbiochem)). After 2 hours, 1 ml of seeding media was added. The next day media was replaced with RPMI/B27 (with insulin). Two days post-seeding, EHTs were removed from PDMS seeding baths and flipped so that the tissue was face-up and not in contact with culture plates to avoid cellular adhesion. Culture media was replaced every 48 hours and EHTs were cultured for up to 23 days. Following recently optimized media conditions, iPSC-CM EHTs were cultured in RPMI/B27 (with insulin) and 100 ng/ml Long R3 IGF-1, 1 mM dexamethasone and 100 nM thyroid hormone (T3).

Optical Coherence Tomography (OCT) to Measure EHT Dimensions

To calculate the stress developed by each EHT, an estimation of the cross-sectional area of each construct is necessary. Cross-sectional area, width, and thickness were measured using optical coherence tomography (FIG. 12A through FIG. 12C). The index of refraction was determined to be 1.38. In every EHT, five evenly spaced images were taken, and the cross-sectional area of each was determined using ImageJ (National Institutes of Health). The five values were averaged to give the mean cross-sectional area. 3D reconstructions of the overall EHT were done using ThorImage OCT software (Thorlabs).

Electrospun Gelatin Scaffolds

The electrospinning setup was similar to that described previously (Eschenhagen, T., et al. Am J Physiol Heart Circ Physiol, 2012, 303:H133-H143). Briefly, an 18 g needle was set up at a distance of 15 cm from the center of a rotating cylindrical collector approximately 15 cm in diameter. The electrospinning solution was derived from that prepared previously (Ma, S. P. & Vunjak-Novakovic, G. J Biomech Eng, 2016, 138: 021010). 10 g of Gelatin (Type B from porcine skin, Sigma) was dissolved in 42 g glacial acetic acid, 21 g ethyl acetate, and 10 g dH2O by heating to 50 C for two hours. This solution was loaded into a syringe and dispensed at 10 µL/min into a 20 kV electric field. Samples were stored at room temperature until use. Crosslinking was performed using 0.5% Glyceraldehyde in 70% Ethanol overnight as described previously[8]. For scanning electron microscopy (SEM), samples were mounted onto SEM stubs with carbon tape, coated with approximately 3 nm of iridium and imaged with a Hitachi SU-70 SEM. For EHT experiments, gelatin scaffolds were laser-cut and were placed into the tissue culture cassettes as described previously and sterilized with 70% Ethanol for one hour. Gelatin scaffolds and concomitant decellularized scaffolds were washed three times in PBS, incubated in DMEM containing 10% FBS for 24 h at 37° C., and then coated overnight with 20 ug/ml Fibronectin solution at 37° C. before seeding.

Mechanical and Functional Testing of EHTs

Figure 5D:
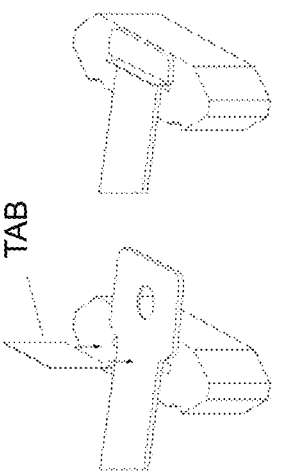
Figure 5E:
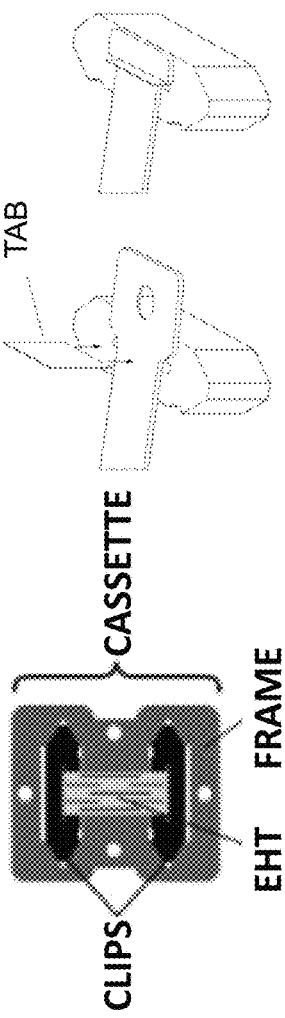

To determine twitch force development and kinetics, EHTs were measured as early as 5 days after seeding. Clips holding the EHT were ejected from the frame and picked up by motorized micromanipulators with claw-like extensions, leaving the muscle suspended between an anchoring attachment claw on one end and a force transducer mounted to a second claw on the other (FIG. 5D). The EHT was immersed in a temperature-controlled perfusion bath equipped with electrodes for field stimulus. Throughout measurements, scaffolds were perfused with freshly oxygenated Tyrode's solution (in mM: NaCl 140, KCl 5.4, $MgCl_2$ 1, HEPES 25, glucose 10, and CaCl 1.8; pH adjusted to 7.35). Used Tyrode's solution was collected in a sealed chamber during testing and checked to ensure adequate consistency of pH. The maximum fluctuation never exceeded 0.05 pH units. All measurements were performed at 35° C. During biomechanical testing, NRVM-EHTs were electrically paced (12 V, 10 ms pulse width at 0.5 Hz) and the resulting twitch force was recorded (FIG. 5E). Human EHTs were paced at 1 Hz. Intracellular calcium concentrations were measured in some constructs using the ratiometric fluorescent indicator Fura-2 AM.

During mechanical testing, EHTs were stretched until reaching their culture length (6 mm) and again after applying 0.1 mm incremental increases until reaching a length of 6.6 mm (representing 10% total stretch). Ten contraction events were recorded and averaged at each level of stretch. The peak stress ($mN/mm^2$) was computed offline by dividing measured force by the cross-sectional area of the EHT. Characteristics of contraction kinetics were also computed offline, including the time to peak stress (TTP) and time from peak stress to 50% relaxation (RT50). The length-stress gain during isometric stretch (slope of the stretch-peak stress relationship, FIG. 13C) was calculated for each scaffold using engineering strain as the unit for stretch. The force-frequency relationship was determined while keeping EHTs at 10% stretch and taking records at 0.5, 1, 2, 4, 6, and 8 Hz. During force-frequency measurements, pacing capture of EHTs was ensured by checking real time oscilloscope readings of the force transducer voltage output.

Ratiometric fluorescent indicator Fura-2 AM. Fura-2 AM loading was achieved by incubating the EHT at room temperature in loading solution (Tyrode's supplemented with 17 µg/ml Fura-2 AM, 0.2% Pluronic F127, 0.5% Cremophor EL, 4.3 µg/mL TPEN) for 20 minutes. The test apparatus was built around an inverted fluorescence microscope (Nikon Ti-U) with an attached ratiometric spectrofluorometry system (RatioMaster, PTI). A central segment of the EHT was placed above a 10× objective, and the sample was excited with a rapidly alternating sequence of 340/380 nm light. Emitted light from the specimen was filtered, and the response centered at 510 nm was recorded by the spectrofluorometer. Custom post-processing routines separated the interleaved excitation response signals and computed a final ratiometric response Inotropic response. To test for a positive inotropic response 100 nM of isoproterenol was added to freshly bubbled Tyrode's solution, which also contained 1 mM of ascorbic acid. Tissues were equilibrated in Tyorde's solution for 30 minutes and measured at 8% stretch. Solutions were changed to isoproterenol containing Tyrode's and the tissue was equilibrated for another 30 minutes before measurements were taken again. Isoproterenol was washed out to confirm that the reversibility of the response.

Shear Loading and Gene Expression Responses in EHTs

Two days after seeding, EHTs were exposed to 10% static shear or 10% stretch loading for 2 hours. This was achieved by removing clipped EHTs from standard culture frames and placing them back into either original or in specially designed shear or stretch frames. When inserted into the shear frame, both clips were forced to rotate by 7.5° about their geometric center. This produced a two-dimensional deformation in the plane of the ribbon-like EHT that equated to a shear strain component of 0.1 (10% shear strain) relative to the fiber direction. Strain in the direction of the fibers remained zero; the fiber length was not changed; therefore, the matrix fibers were pulled (sheared) past each other when EHTs were mounted in this configuration. Relative changes in gene expression were quantified using Real Time-quantitative PCR. Brain natriuretic peptide (BNP), a transcript belonging to the fetal or hypertrophic gene program was quantified relative to the housekeeping gene glyceraldehyde 3-phosphate dehydrogenase (GAPDH). Real-time quantitative PCR. To assess relative changes in gene expression, real-time quantitative PCR was performed EHTs were removed from the tissue culture cassette using a dissecting microscope, submerged in Trizol reagant (Invitrogen), and homogenized using a Precellys (LeGrice, I. J., et al. Circ Res, 1995, 77:182-193) bead beater (Bertin Technologies). RNA was isolated using a standard procedure (Hoshijima, M. Am J Physiol Heart Circ Physiol, 2006, 290:H1313-25) followed by a DNAse I digestion treatment (Turbo DNAfree, Ambion). Nucleic Acid Purity was assessed using a nanoDrop spectrophotometer (Thermo Scientific). Reverse transcription (using a High capacity cDNA Reverse Transcription Kit, Applied Biosystems) was be done in the presence of RNAse inhibitor (Applied Biosystems) to synthesize high quality cDNA. Changes in BNP and GAPDH were quantified by real-time PCR using the iQ SYBR Green Supermix (Biorad) using PrimePCR primers (BioRad) for NRVM scaffolds and customized primers for human genes (as shown below). Gene expression was determined through delta-delta CT method (Lin, D. H. & Yin, F. C. J Biomech Eng, 1998, 120:504-517).

Histological Evaluation of EHTs

For immunofluorescence, EHTs were fixed in 4% PFA while being kept at culture length in the standard culture cassettes for 2 hours at room temperature. After the fixation step, EHTs were washed in PBS twice and carefully removed from the clips using a dissecting scope. For phalloidin staining, the entire EHT sample was incubated in 1:100 Phalloidin (Alexa Fluor 568—Life Technologies Catalog #A12380) diluted in PBST (0.1% Tween 20 in PBS) for 30 minutes, and then washed in PBS for 3×2 minutes. For all other stains, antigen retrieval was necessary. Fixed tissues were incubated in a 95° C. hot sodium citrate buffer (10 mM Sodium Citrate, 0.05% Tween 20, pH 6.0) in a water bath at 90° C. or 20 minutes. The entire EHT sample was cooled at room temperature for 20 minutes before washes in PBST for 2×2 minutes. EHTs were blocked for 30 minutes in PBST containing 10% [vol/vol] goat serum. Subsequently, EHTs were incubated with 1:100 anti Connexin-43 rabbit polyclonal antibody (Catalog #C6219, Sigma-Aldrich) and 1:100 anti-Troponin T mouse monoclonal antibody (Catalog # MS295, P Fisher Scientific) for 24 h at 4° C. Three washes with PBST were performed before incubating in 1:250 Alexa Flour 488 goat anti-mouse IgG (H+L, Catalog #A11029, Life technologies) and 1:250 Alexa Flour 568 goat anti-rabbit IgG (H+L, Catalog #A11036, Life technologies) for 1 h at room temperature. Following secondary antibody incubation, EHTs were washed in PBS 3×2 minutes and coverslipped using DAPI containing fluoroshield mounting media (Catalog #F6057, Sigma-Aldrich). All imaging was performed using a Leica LSM 510 system.

Statistical Analysis

Comparisons involving two groups were made using Student's t-test (unpaired), whereas multiple comparisons between groups were performed by one- or two-way analysis of variance (ANOVA) with the Tukey post hoc test as indicated. The threshold for statistical significance was set at $p<0.05$. Means are reported with SEM unless stated otherwise.

Results

Spontaneous beating and remodeling of EHTs. Testing and characterization of laser-cut decellularized myocardial scaffolds was performed using NRVMs as a cell source (unless otherwise noted). Regions of spontaneous beating within the constructs were observed two days post-seeding, transitioning to synchronously contracting constructs at approximately day five. EHT morphology and remodeling were followed over time using OCT imaging (FIG. 12A). Measurements in 9-, 16-, and 23-day-old EHTs show a reduction in cross-sectional area of the tissue with age (FIG. 12A, FIG. 12C). More detailed tracking of EHT dimensions from day 3 to day 16 shows that remodeling starts immediately, with thickness of the tissue increasing until day 9. The EHTs acquired an hourglass shape and circular cross-section of approximately 250 µm in diameter by day 16 (FIG. 11D and FIG. 12B). Matrix compaction and tissue remodeling slowed down significantly around day 12 (FIG. 12B). Histological analysis confirms maturation of cardiac components. Histological analysis of NRVM EHTs at day 16 showed that cells in the EHT were distributed evenly throughout the constructs (FIG. 17A, FIG. 17B). Furthermore, sections stained for myofilament proteins exhibited a striated pattern that indicated the presence of organized sarcomeres (FIG. 12D). Fluorescent staining for Connexin 43 in EHTs seeded with hESC-derived cardiomyocytes showed that the cells had also formed gap junctions, indicating electrical coupling of individual cardiomyocytes (FIG. 12E). Time in culture improves cardiac maturation. A series of experiments were performed to demonstrate the potential of this system for biomechanical and functional characterization of engineered myocardium. First, to determine the effects of culture time on stress development and twitch kinetics, scaffolds were tested after either 9, 16 or 23 days in culture (n=11, 8 and 12 respectively; FIG. 13A through FIG. 13C). Time in culture significantly impacted EHT peak twitch stress (one-way ANOVA, $p<0.05$). Between day 9 and day 23, peak stress increased 2.4 fold (from 0.20±0.03 to 0.49±0.08 mN/mm2, FIG. 13B). Furthermore, the sensitivity of peak stress to stretch (Frank-Starling response) increased significantly with time in culture (length-stress gain, $p<0.01$, FIG. 13C). Twitch kinetics, as measured by time to peak stress (TTP) and time from peak stress to 50% relaxation (RT50), did not change significantly with culture time (FIG. 18A). A negative force-frequency response was observed (FIG. 18B).

Thyroid hormone speeds contractile kinetics. To assess the sensitivity of this system towards changes in contractility and twitch kinetics, EHTs were subjected to a pharmacological perturbation known to alter the intrinsic properties of cardiac muscle. In rodents, an increase in thyroid hormone (T3) promotes expression of the faster α isoform of myosin heavy chain23. Hence, EHTs were treated in culture for 15 days with T3 (10 ng/ml, FIG. 13D through FIG. 13F) and tested repeatedly in a longitudinal study. EHTs were characterized functionally and then returned to culture conditions at days 5, 8, 12, and 15. T3 had no significant effect on the evolution of peak stress development across time points (2-way repeated measures ANOVA) (FIG. 13E). However, T3 treatment significantly accelerated rates of contraction and relaxation at every time point analyzed in comparison to the non-treated control (T3 treatment n=10, no treatment n=12; $p<0.001$, FIG. 13F and FIG. 12). After 15 days in culture, EHTs treated with T3 had a TTP of 77±2 ms in comparison to 113±6 ms and a RT50 of 63±3 ms versus 130±3 ms in untreated samples.

Figures 14A, 14B, 14C, 14D, 14E:
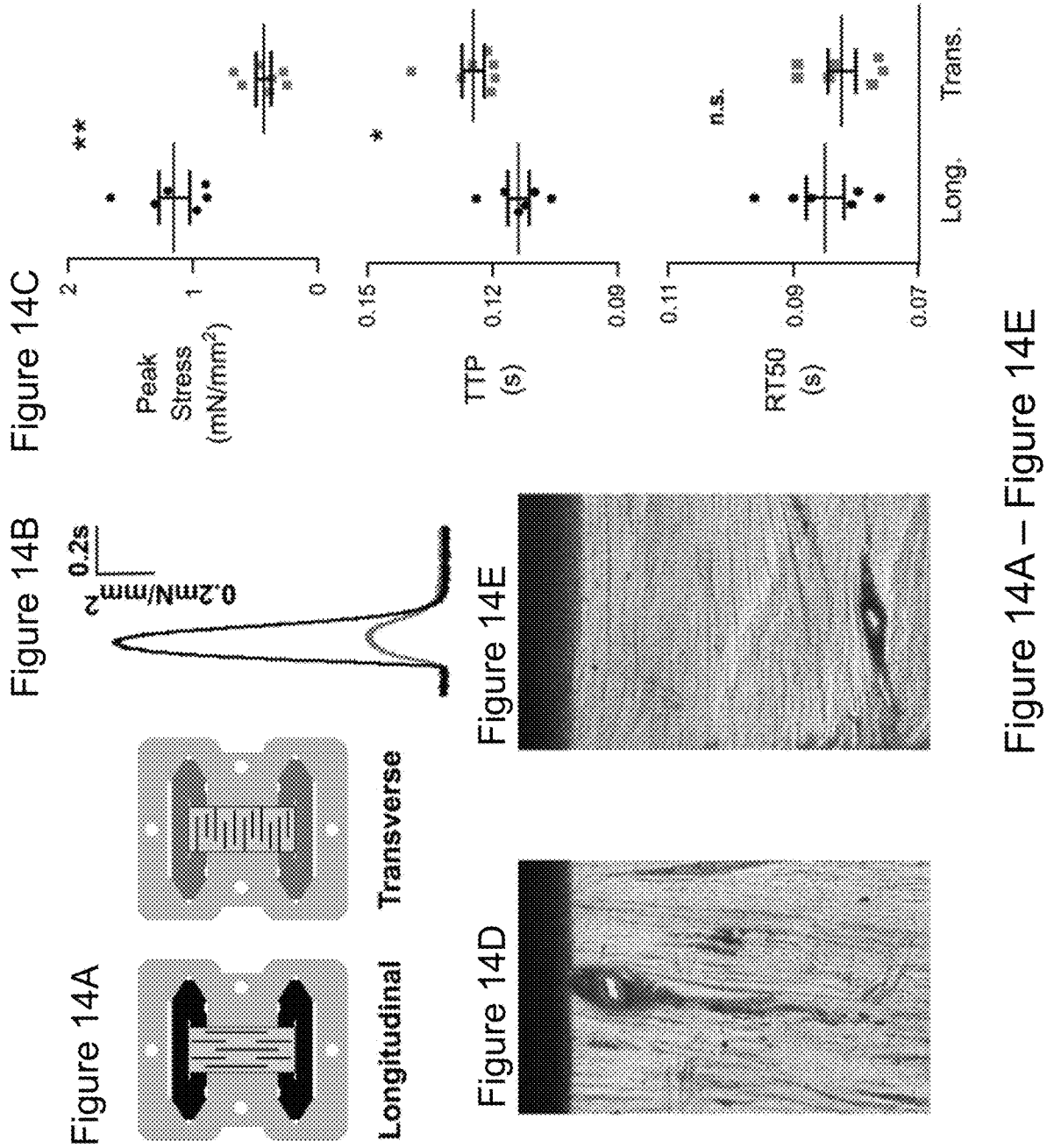
FIG. 14A through FIG. 14E illustrate anisotropic twitch behavior in seeded EHTs.

NRVMs produce less force when grown in scaffolds with transversely oriented fibers. The fiber direction in native cardiac tissue is visible with the naked eye (FIG. 14D, FIG. 14E). A major advantage of scaffolds laser-cut from native myocardium is the ability to easily control fiber orientation of the matrix material. To determine whether embedded cells would follow the alignment cues provided by the matrix of the EHT, tissues were cut such that the native fiber angle was oriented either parallel to the long axis of the construct (longitudinal, FIG. 14A, FIG. 14D) or 90 degrees relative to the long axis (transverse, FIG. 14A, FIG. 14E). Longitudinal and transverse scaffolds were seeded and cultured for 6 days prior to biomechanical characterization. When function was assessed at 10% stretch, longitudinal scaffolds (n=6) produced on average a peak stress that was 240% greater than transverse controls (n=7) under the same conditions ($p<0.001$, FIG. 14B, FIG. 14C). TTP was 11% longer in transverse EHTs ($p<0.05$, FIG. 14C), while no difference in the rate of relaxation was observed. To further assess whether the natural structure, biochemical composition, and density of the native scaffold provide unique advantages to EHT function, EHTs made from laser-cut decellularized myocardium were also compared with tissues made from anisotropic electrospun gelatin scaffolds (FIG. 20A through FIG. 20D). To facilitate comparison, both scaffold materials were coated with fibronectin prior to cell seeding. At day 9 post-seeding, both tissues exhibited a positive Frank-Starling response. However, decellularized myocardial scaffolds produced significantly higher peak twitch stresses (FIG. 20D). BNP expression is stimulated by fiber stretch but not shearing stretch. Laser-cut EHTs with controlled fiber orientations enable the study of novel mechanical perturbations and the cellular signaling cascades they may activate. Responses of the tissue to shear strain in an in vitro system is of particular interest since the ventricular myocardium is exposed to shear loading throughout the cardiac cycle (LeGrice, I. J., et al. Circ Res, 1995, 77:182-193), which varies according to myocardial transmural depth (Feigl, E. O. & Fry, D. L. Circ Res, 1964, 14:536-540). Loading regimes in vivo are complex and contain varying shear and stretch components making it difficult to separate the individual responses. This in vitro system allows the application of unambiguously defined mechanical loads, including the ability to apply pure stretch and shear separately. To determine the effects of shear loading on cardiac gene expression, two-day old NRVM EHTs were exposed to static 10% stretch applied for two hours, either along the fiber direction (n=18), at an angle such that fibers were sheared past each other while remaining at roughly constant length (n=22), or as a control at original culture length (n=16) (FIG. 15A). The two-day-old initial time point was chosen because EHTs at this stage have remodeled minimally, and their ribbon-like shape allows the clean application of a shearing stretch. After two hours, fiber stretch and shear stretch had elicited significantly different responses with regard to BNP expression ($p<0.05$, FIG. 15B). As expected, fiber stretch led to increased BNP expression, but surprisingly no expression change in the sheared tissues with respect to non-stretched control was observed. The differential response to stretch vs. shear loading was confirmed in separate experiments using EHTs formed with cardiomyocytes derived from human induced pluripotent stem cells (hiPSC-CMs, FIG. 15B). Detailed fold-change values can be found in FIG. 23.

Figure 16A:
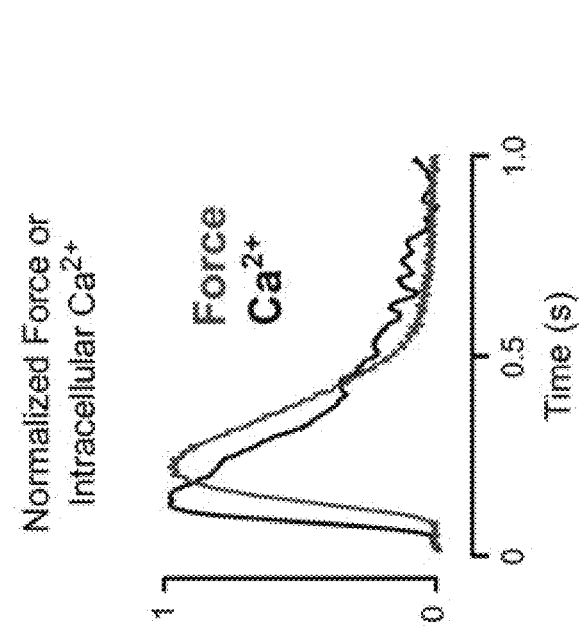
FIG. 16A through FIG. 16D depict EHTs seeded with human-derived cardiomyocytes.
Figure 16B:
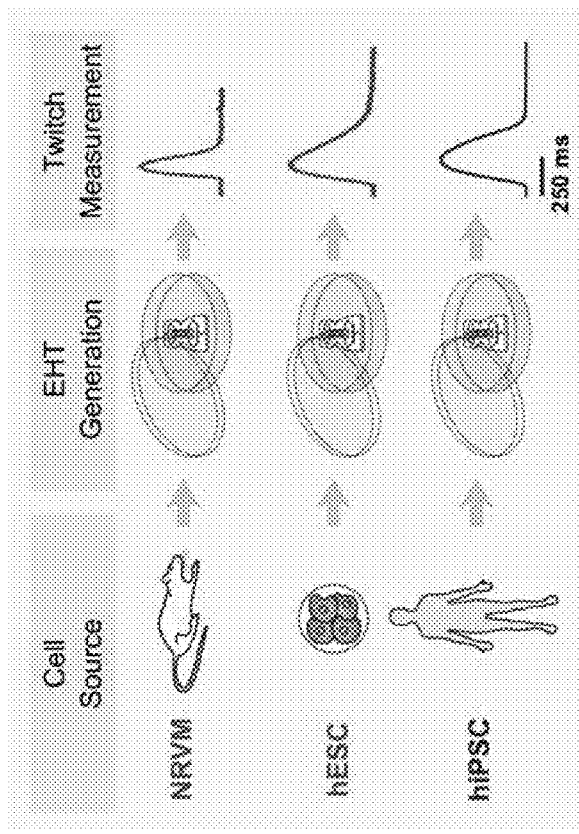

Laser-cut decellularized myocardium can be used for biomechanical characterization of human iPSC-derived cardiomyocytes. To determine whether the method could be readily applied to human-derived cells, decellularized scaffolds were also seeded with cardiomyocytes derived from human embryonic cells (hESC-CM) or hiPSC-CMs (FIG. 16A). Using standard media conditions, hESC-CMs produced beating scaffolds with measurable intracellular Ca2+ transients and maximum twitch stress of 1.7 mN/mm$^2$ at day 16 (n=3) (FIG. 16B). Scaffolds seeded with hiPSC-CM (obtained from a healthy donor) were cultured in media containing thyroid hormone, IGF-1, and the glucocorticoid analog dexamethasone, factors recently shown to promote cardiomyocyte maturation (Birket, M. J. et al. Cell Rep, 2015, 13:733-745). hiPSC-CM EHTs produced an average peak stress (force divided by cross-sectional area) of 2.2±0.76 mN/mm$^2$ at 8% stretch, with maximum peak stress of 6.5 mN/mm2 (n=8, FIG. 16D). The magnitude of raw force, for purposes of comparison, was an average of 0.3±0.09 mN. One of the hiPSC-CM EHTs achieved a maximum peak force of 0.86 mN. Assessing the kinetics of these constructs showed a RT50 of 168±10 ms and a TTP of 181±12 ms (at a 1 Hz pacing frequency). hiPSC-CM EHTs also responded to the β-adrenergic agonist Isoproterenol by showing appropriate lusitropic behavior (shorter TTP and RT50) (FIG. 21A, FIG. 21B).

The data presented here demonstrate that laser-cut decellularized myocardium can function as an effective scaffold for engineered heart tissue. This method takes advantage of the natural anisotropy of cardiac ECM while permitting creation of macroscopic customized shapes that are suitable for measurement of contractile force and other experiments. Some of these, such as the assessment of fiber shear effects on BNP production, are unique among in vitro studies. Laser-cut decellularized myocardial scaffolds also proved to be versatile platforms for EHT creation, producing viable tissues from NRVMs, hESC-CMs, and hiPSC-CMs alike. This suggests that the approach could be useful in a variety of applications, including physiological characterization of patient-derived cardiomyocytes and in vitro studies of cardiomyocyte mechanotransduction and remodeling.

The observation that shearing stretch tended to decrease BNP expression is surprising, as it is typically seen as a stretch-induced factor. Studies have shown that biaxially stretched cardiac cells increase BNP production (Frank, D. et al., Hypertension, 2008, 51: 309-318). This coincides straightforwardly with its traditional physiological role as a volume-regulating hormone, promoting diuresis in response to excess ventricular filling (Nishikimi, T., et al., Cardiovasc Res, 2006, 69:318-328). In line with this concept, the constructs did increase BNP expression when subjected to fiber stretch (FIG. 15B). The shear experiment suggests an alternate mechanism that could allow BNP transcription to be triggered not just by increased preload, but by increased afterload as well. Fiber shearing during systole is a large component of normal myocardial deformation, and is observed at the organ level as ventricular torsion. It has been shown that increased afterload can reduce cardiac torsion during systole by as much as 10% (Dong, S. J. et al., Am. J. Physiol. 277, 1999:H1053-60), which by extension may decrease fiber shear by a similar amount. If BNP transcription is enhanced by the absence of shear, as measurements suggest, it would therefore constitute a new mechanism by which cells could sense changes in arterial loading (afterload reflex). This could be seen as being in line with recent clinical findings, where reduced left ventricular global longitudinal strain in patients with chronic heart failure was associated with increased plasma concentrations of N-terminal-pro-brain-natriuretic-peptide (Gaborit, F. et al., BMC Cardiovasc Disord, 2015, 15: 92). Similarly, such a mechanism could explain why patients with systemic hypertension show elevated BNP levels in the absence of heart failure (Law, C., et al. Congest Heart Fail, 2010, 16:221-225).

Another novel insight provided by the technology described herein is that neonatal or fetal-like cardiomyocytes respond more potently to local matrix cues for alignment than to macroscopic loading (FIG. 14A through FIG. 14E). In systems that use isotropic gels as scaffold material, cells appear to align in the direction of greatest stiffness or applied loads (Simon, D. D., et al. Journal of the Mechanical Behavior of Biomedical Materials 2012, 14:216-226, Costa, K. D., et al. Tissue Eng., 2003, 9:567-577). Hence, to achieve anisotropy in hydrogel-based tissues, externally applied boundary loads appear to be required (Costa, K. D., et al. Tissue Eng. 2003, 9:567-577; Lee, E. J., et al. Annals of Biomedical Engineering, 2008, 36:1322-1334; Black, L. D., et al. Tissue Engineering Part A, 2009, 15: 3099-3108). Cells are provided with a scaffold that contains the natural fiber structure. It was determined that in transversely oriented scaffolds the muscle cells exhibited slower twitch kinetics and produced only a fraction (~30%) of the peak tension observed in longitudinally-oriented samples. It is interesting to note that similar behaviour has been shown in native cardiac muscle tissue preparations. For instance, Lin and Yin (Lin, D. H. & Yin, F. C. J Biomech Eng, 1998, 120:504-517) showed that barium-induced contractures of rabbit myocardium produce roughly 50% less active force in the cross-fiber direction than in the fiber direction. It therefore appears that native scaffolding guides cells to produce a realistic anisotropy in active contractile properties. When compared to anisotropic electrospun gelatin scaffolds, laser-cut decellularized myocardium showed stronger peak stresses and a tendency toward faster twitch kinetics. This suggests that the biochemical and biomechanical cues found in the decellularized native myocardium confer specific advantages to the process of in vitro tissue formation over and above those achieved through anisotropic synthetic scaffolds.

There is a large and diverse body of methods for the generation of engineered heart tissue, each one with benefits for specific applications (Hirt, M. N., et al. Circ Res, 2014 114:354-367; Ma, S. P. & Vunjak-Novakovic, G. J Biomech Eng, 2016, 138: 021010). Other methods fall into two broad categories: macroscopic bulk tissue constructs (Black, L. D., et al. Tissue Engineering Part A, 2009, 15:3099-3108; Bian, W., et al. Nature Protocols, 2009, 4:1522-1534; Hirt, M. N. et al. Basic Res Cardiol, 2012, 107:307-16; Tulloch, N. L. et al. Circ Res, 2011, 109:47-59; Cashman, T. J., et al. PLoS ONE, 2016 11: e0146697) and microfabricated cell assemblies (microtissues or 'heart on a chip' approaches) (Grosberg, A., et al. Lab Chip, 2011, 11:4165-4173; Boudou, T. et al. Tissue Engineering Part A, 2012, 18:910-919; Huebsch, N. et al. Sci Rep, 2016, 6:24726).

Macroscopic constructs have the advantage of being large enough to produce contractions that can be measured directly with traditional force transducers. In contrast, measuring force in microtissues requires that they be attached to a deformable elastic structure of known stiffness. Substrate deformation allows the force to be inferred, but also means that substantial muscle shortening is always a component of such measurements. Twitches recorded in macroscopic preparations can be characterized under isometric conditions that essentially eliminate length dependent effects and provide high fidelity, high-resolution characterizations of active stress generation.

Microtissues on the other hand require fewer cells, have smaller dimensions, and can achieve anisotropy by direct micropatterned cues. The small form factor can be a key consideration due to the oxygen diffusion limit for physiological tissue. Constructs thicker than ~200 µm that are seeded with physiological cell densities can exhibit poor cell viability due to nutrient and oxygen exchange problems at their core (Radisic, M. et al. Biotechnol. Bioeng., 2006, 93:332-343). Cardiac microtissues typically have a cross-sectional area of 0.01 $mm^2$ with a diameter not exceeding 70 µm, the equivalent to just a few cells (Boudou, T. et al. Tissue Engineering Part A, 2012, 18:910-919). This is far thinner than typical fibrin- or hydrogel-based EHTs, where the average diameter is ~800 µm (Zimmermann, W. H. et al. Circ Res, 2001, 90:223-230) and cross-sectional areas are typically ~1 $mm^2$ (Turnbull, I. C. et al. The FASEB Journal, 2014, 28:644-654). Beyond the diffusion advantage, some microtissues are grown on patterned anisotropic substrates that impart improved Ca2+ handling, excitation-contraction coupling, alignment, and peak force (Feinberg, A. W. et al. Biomaterials, 2012, 33:5732-5741; Pong, T. et al. Experimental Biology and Medicine, 2011, 236:366-373).

Figure 16C:
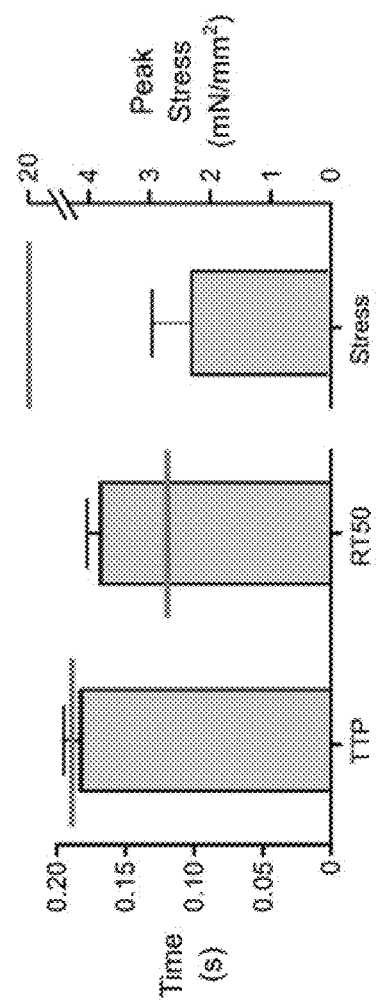
Figure 16D:
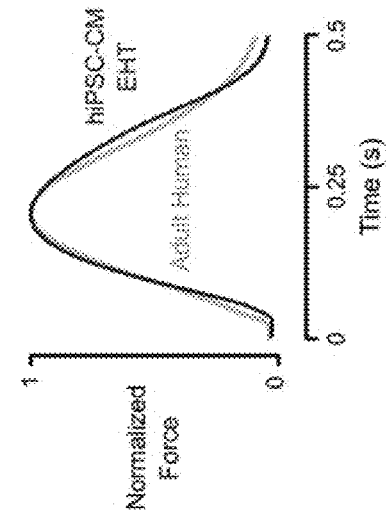
Figure 19:
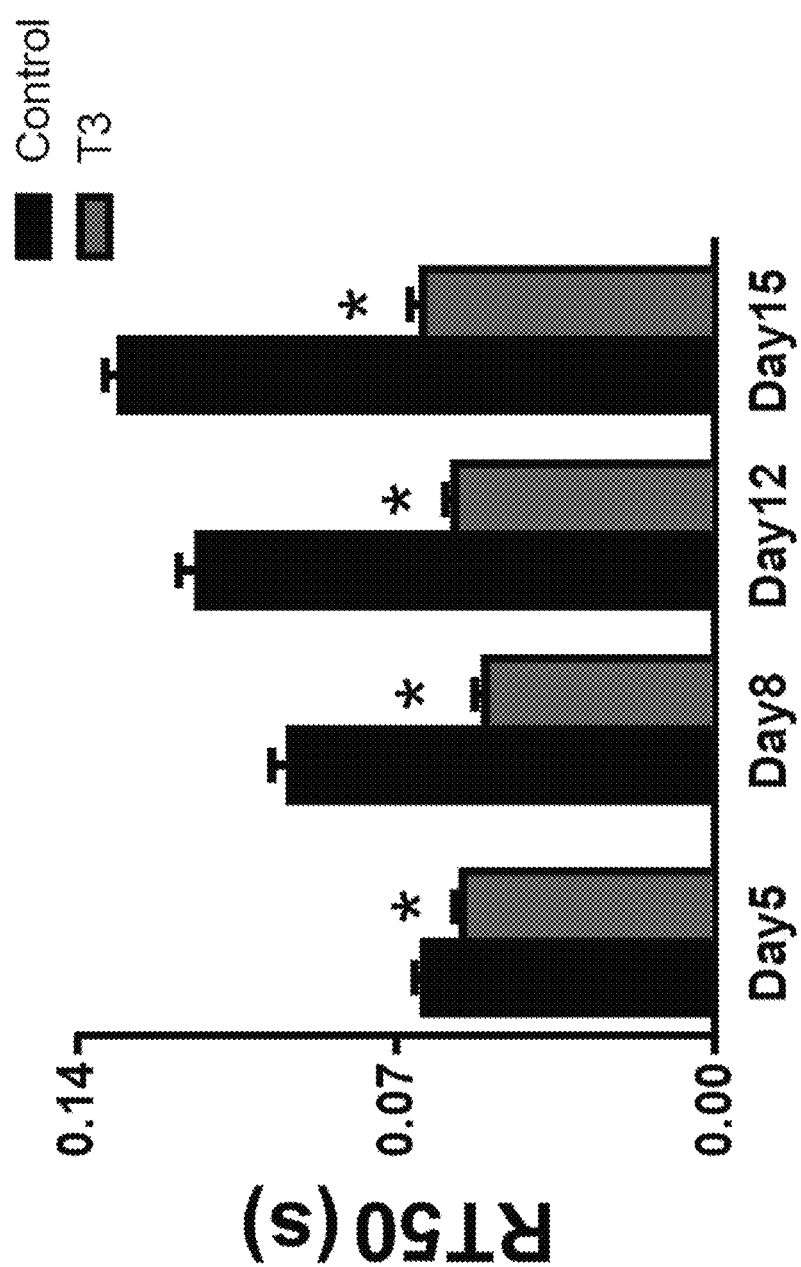
FIG. 19 depicts the results of experiments demonstrating the effects of T3 on relaxation. Measurements of relaxation time (RT50) in T3 treated (teal, n=10)/non treated (black, n=12) laser-cut EHTs. All results were obtained from NRVMs seeded into laser-cut decellularized porcine myocardium.

The laser-cut decellularized matrix approach presented here can be seen as a compromise between macroscopic and microfabricated EHTs—the constructs described herein are large enough to have robust contractile forces while possessing a thin, realistically anisotropic form. By starting with native myocardium, thin but structurally stable anisotropic scaffolds can be cut. After 16 days in culture, EHTs had an average diameter of 250 µm and cross-sectional area of ~0.1 $mm^2$, substantially smaller than typical macroscopic constructs. Peak stresses produced by the NRVM EHTs were ~1 $mN/mm^2$ on average and reached 3 $mN/mm^2$ in some cases. These values are directly comparable to others in the field, who reported average stress within the 0.1-4 $mN/mm^2$ range, with the highest reported stress to date being 9 $mN/mm^2$ (Hirt, M. N., et al. Circ Res, 2014 114:354-367; Bian, W., et al. Nature Protocols, 2009, 4:1522-1534). As a point of reference, isolated neonatal rat trabeculae show peak stress of around 8-9 mN/mm2 (Moreno-Gonzalez, A. et al. J Mol Cell Cardiol, 2009, 47:603-613) and thin adult rat trabeculae of about 42 mN/mm2 (Raman, S., et al. Pflugers Arch—Eur J Physiol, 2006, 451: 625-630). In the case of the iPSC-CM EHTs described herein, peak stresses averaged to ~2.2 $mN/mm^2$ putting them within commonly reported values (Hirt, M. N. et al. J Mol Cell Cardiol, 2014, 74:151-161; Hirt, M. N. et al. J Mol Cell Cardiol, 2014, 74:151-161; Turnbull, I. C. et al. The FASEB Journal, 2014, 28:644-654) but below intact left ventricular muscle strips (FIG. 16D).

Although improvements in peak stress are still needed, it is interesting to note that the NRVM EHTs described here are nonetheless approaching near-native twitch kinetics. In 15 days old EHTs after T3 treatment, the measured RT50 of around 59 and TTP of 83 ms (2 Hz) are similar to those reported for thin native rat trabeculae (45 and 75 ms respectively at a pacing frequency of 2 Hz (Raman, S., et al. Pflugers Arch—Eur J Physiol, 2006, 451: 625-630)). The only other study to report both TTP and RT50 in NRVM based 2-week old EHTs was the work of Morgan et al. (Morgan, K. Y. & Black, L. D. J Tissue Eng Regen Med, 2014, doi: 10.1002/term. 1915). Their reported RT50 and TTP values (125 and 150 ms respectively at 0.5 Hz pacing) are notably slower than those observed in the method described herein. This difference could potentially be explained by the T3 media substitution (Yang, X. et al. J Mol Cell Cardiol, 2014, 72:296-304).

Ensuring that EHTs recapitulate adult myocardial function as closely as possible remains a primary concern as the field seeks to use human engineered constructs for preclinical drug screening and patient-specific disease modeling (Cashman, T. J., et al. PLoS ONE, 2016, 11: e0146697; Huebsch, N. et al. Sci Rep, 2016, 6, 24726; Hinson, J. T. et al. Sci, 2015, 349:982-986). Animal studies have already demonstrated that the effects of sarcomeric mutations depend on the isoform profile of other proteins in the sarcomere (Ford, S. J., et al. J Mol Cell Cardiol, 2012, 53:542-551), something that varies substantially during maturation (Schwan, J. & Campbell, S. G. Biomark Insights, 2015, 10:91-103). One way to gauge the overall maturation of EHTs is to perform detailed characterization of their twitch kinetics (Turnbull, I. C. et al. The FASEB Journal, 2014, 28:644-654). Using an optimized media formulation recently reported by another group (Birket, M. J. et al. Cell Rep, 2015, 13:733-745), human EHTs were created with twitch morphology essentially equivalent to human right ventricular trabeculae (Milani-Nejad, N. & Janssen, P. M. Pharmacol. Ther., 2014, 141:235-249) (FIG. 16C). Left ventricular muscle strips seem to possess slightly faster kinetics (Mulieri, L. A., et al. Circulation, 1992, 85:1743-1750), but hiPSC-CM EHTs are beginning to approach even these values (FIG. 16D). Maturation in the constructs described herein could be further improved by applying an electrical pacing regime in culture just above the intrinsic beating frequency (Godier-Furnémont, A. F. G. et al. Biomaterials, 2015, 60:82-91).

In conclusion, the method described herein for generating artificial cardiac tissue joins several others that have been developed in recent years. Evaluating the utility of any given approach depends as much on the intended use of the EHT as it does on any particular metric of performance. In addition to standard isometric twitch behavior, which is extremely robust in the constructs, this approach makes possible for the first time new biomechanical assays in which properties of the tissue can be assessed in relation to realistic structural and functional anisotropy. As such, it provides a platform for mechanotransduction studies that are not currently served by any other approach. Although the focus is on decellularized native myocardial scaffolds, the tissue culture cassette system was easily adapted for use with synthetic laser-cut electrospun scaffolds (FIG. 20A), demonstrating that the overall cassette approach could be adapted to accommodate a wide variety of scaffold types. Because the system can be used to form functional tissue from cultured human embryonic as well as induced pluripotent—stem cell derived cardiomyocytes, ultimately finding use in patient-specific in vitro modeling. For inherited disorders such as familial hypertrophic cardiomyopathy, where tissue remodeling, mechanotransduction, and contractile mechanics play prominent roles, this platform is a suitable alternative to current methods.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A cassette device for securing a tissue sample, the device comprising:
   a frame having a top surface with a first clip slot in the top surface and a second clip slot in the top surface, wherein the first and second clip slots are separate from each other;
   a first clip having a top surface with a slit in the top surface and sized and configured to fit within the first clip slot with the top surface exposed from the first clip slot;
   a second clip having a top surface with a slit in the top surface and sized and configured to fit within the second clip slot with the top surface exposed from the second clip slot;
   a first tab sized and configured to fit within the slit of the first clip; and
   a second tab sized and configured to fit within the slit of the second clip;
   wherein a tissue sample is securable between the first and second clips; and
   wherein the first and second tabs are constructed from a swellable material, and wherein the first tab is configured to securely lock the tissue sample to the first clip, and the second tab is configured to securely lock the tissue sample to the second clip.

2. The cassette device of claim 1, further comprising a tissue sample having a first end and a second end, wherein the first end of the tissue sample is configured to be releasably secured between the first clip and the first tab via a friction fit of the first tab within the slit of the first clip, and the second end of the tissue sample is configured to be releasably secured between the second clip and the second tab via a friction fit of the second tab within the slit of the second clip.

3. The cassette device of claim 1, wherein the tabs have a cylindrical shape.

4. The cassette device of claim 1, wherein the swellable material comprises a hydrogel.

5. The cassette device of claim 1, wherein the first and second tabs further include an inner core comprising a length of polytetrafluoroethylene (PTFE) tube.

6. The cassette device of claim 2, wherein the tissue sample-comprises a sample of decellularized tissue.

7. The cassette device of claim 2, wherein the tissue sample comprises cardiac tissue.

8. The cassette device of claim 7, wherein the cardiac tissue is ventricular wall tissue.

9. The cassette device of claim 2, wherein the first clip and the second clip are removable from the cassette device with the tissue sample remaining suspended between each of the two clips.

\* \* \* \* \*